(12) United States Patent
Kobayashi

(10) Patent No.: US 7,440,661 B2
(45) Date of Patent: Oct. 21, 2008

(54) CONFIGURATION DETECTION DEVICE FOR ENDOSCOPE

(75) Inventor: Shotaro Kobayashi, Saitama (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 11/562,743

(22) Filed: Nov. 22, 2006

(65) Prior Publication Data
US 2007/0116415 A1 May 24, 2007

(30) Foreign Application Priority Data
Nov. 24, 2005 (JP) ............................. P2005-338528

(51) Int. Cl.
*G02B 6/06* (2006.01)
(52) U.S. Cl. ..................... 385/117; 385/12; 385/13; 600/117
(58) Field of Classification Search ............... None
See application file for complete search history.

(56) References Cited

U.S. PATENT DOCUMENTS

| | | | | | |
|---|---|---|---|---|---|
| 5,097,252 | A | * | 3/1992 | Harvill et al. | 340/540 |
| 5,253,647 | A | | 10/1993 | Takahashi et al. | |
| 5,316,017 | A | * | 5/1994 | Edwards et al. | 600/595 |
| 5,321,257 | A | * | 6/1994 | Danisch | 250/227.16 |
| 5,633,494 | A | * | 5/1997 | Danisch | 250/227.16 |
| 6,127,672 | A | * | 10/2000 | Danisch | 250/227.14 |
| 6,203,493 | B1 | * | 3/2001 | Ben-Haim | 600/117 |
| 6,471,710 | B1 | * | 10/2002 | Bucholtz | 606/130 |
| 6,563,107 | B2 | * | 5/2003 | Danisch et al. | 250/227.14 |
| 6,600,861 | B2 | * | 7/2003 | Furusawa et al. | 385/116 |
| 6,656,110 | B1 | * | 12/2003 | Irion et al. | 600/117 |
| 6,832,985 | B2 | * | 12/2004 | Irion et al. | 600/118 |
| 6,846,286 | B2 | * | 1/2005 | Suzuki et al. | 600/145 |
| 7,209,605 | B2 | * | 4/2007 | Cantin et al. | 385/12 |
| 2005/0041905 | A1 | * | 2/2005 | Lagakos et al. | 385/12 |
| 2005/0281520 | A1 | * | 12/2005 | Kehoskie et al. | 385/117 |

FOREIGN PATENT DOCUMENTS

| | | |
|---|---|---|
| JP | 2793881 | 6/1998 |
| JP | 3373055 | 11/2002 |

OTHER PUBLICATIONS

U.S. Appl. No. 11/557,510 to Sugimoto et al., which was filed on Nov. 8, 2006.

* cited by examiner

*Primary Examiner*—Sung Pak
*Assistant Examiner*—Chad H Smith
(74) *Attorney, Agent, or Firm*—Greenblum & Bernstein, P.L.C.

(57) ABSTRACT

A configuration detection device includes a light-providing optical fiber, a light reflector a curvature-detecting optical fiber, and a light modulator. The light-providing optical fiber transmits detection light in a plurality of wavelength ranges that have different wavelengths from one another, The light reflector reflects the detection light as reflected light. The curvature-detecting optical fiber transmits the reflected light, and is bent together with an endoscope. The light modulator modulates at least one of the strength or the wavelength of the reflected light for each of the wavelength ranges. Based on at least one of the strength or the wavelength of the reflected light that is pre-modulated and post-modulated, and based on the distance between the light modulator and the output end of the curvature-detecting optical fiber, the configuration of the endoscope is detectable.

12 Claims, 23 Drawing Sheets

FIG. 4
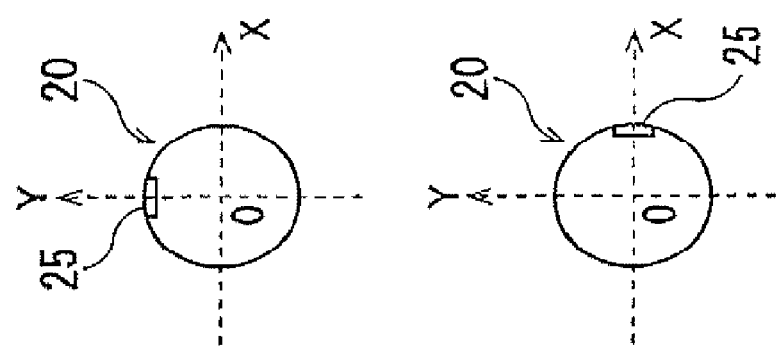
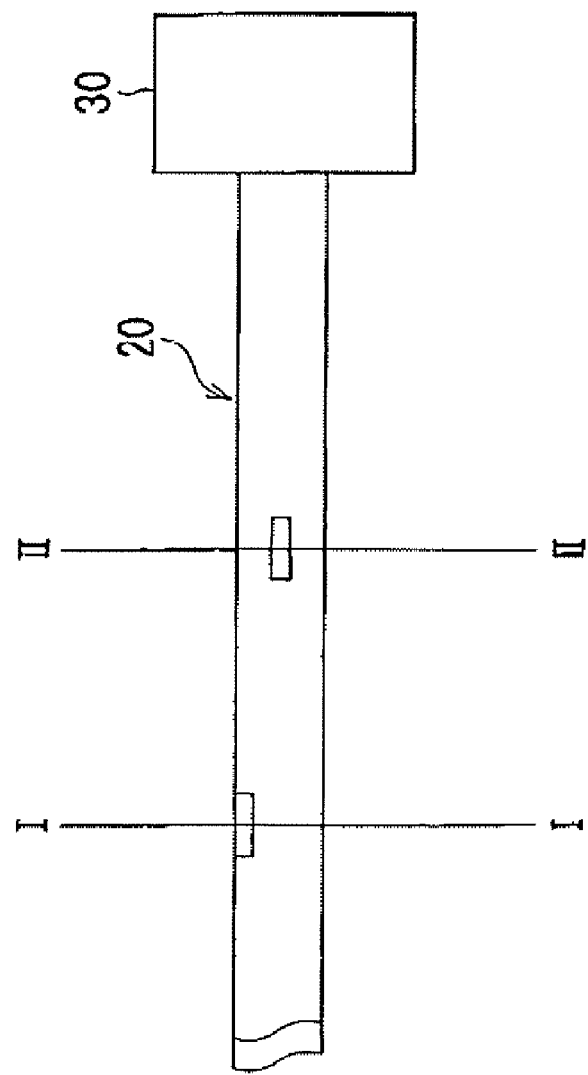

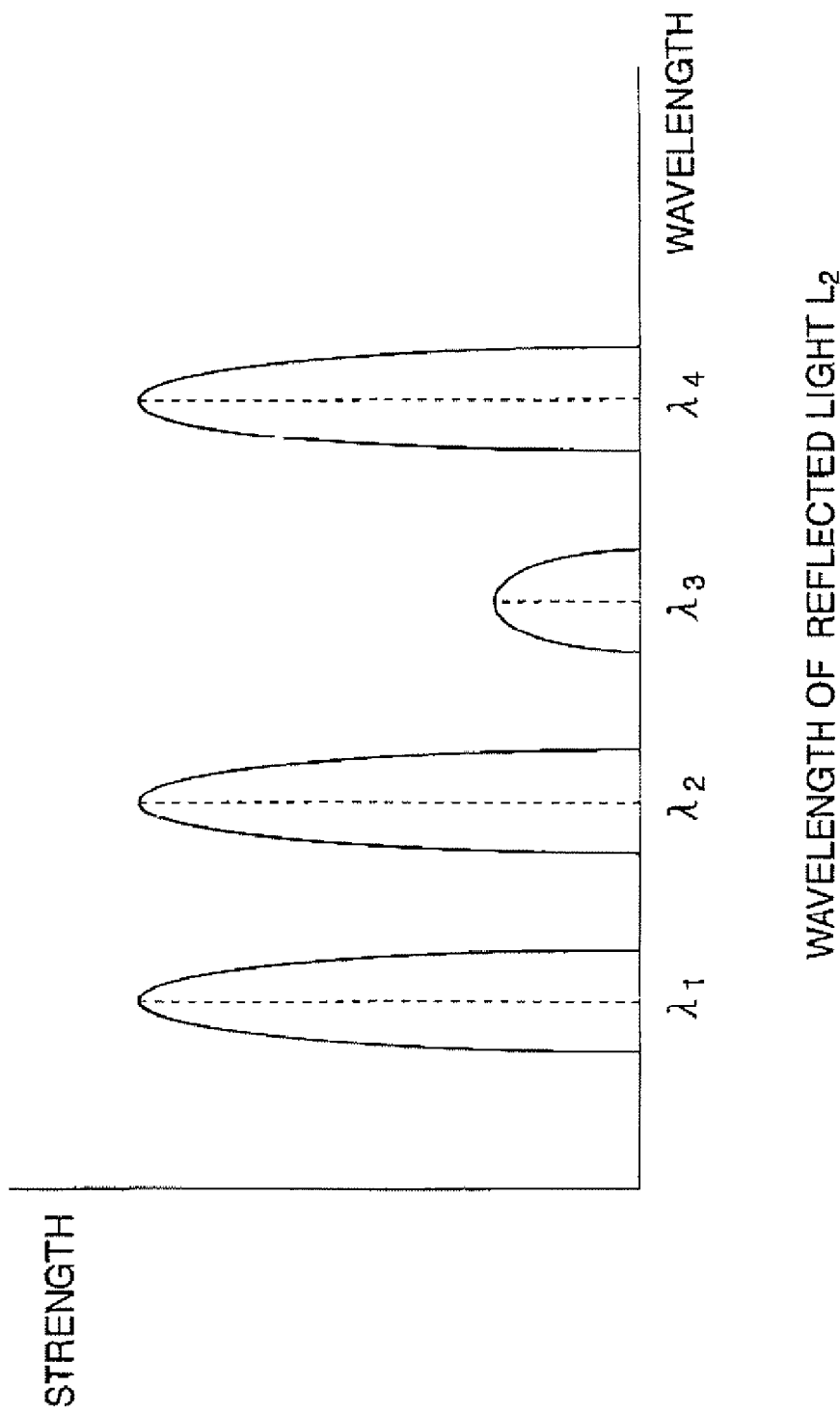

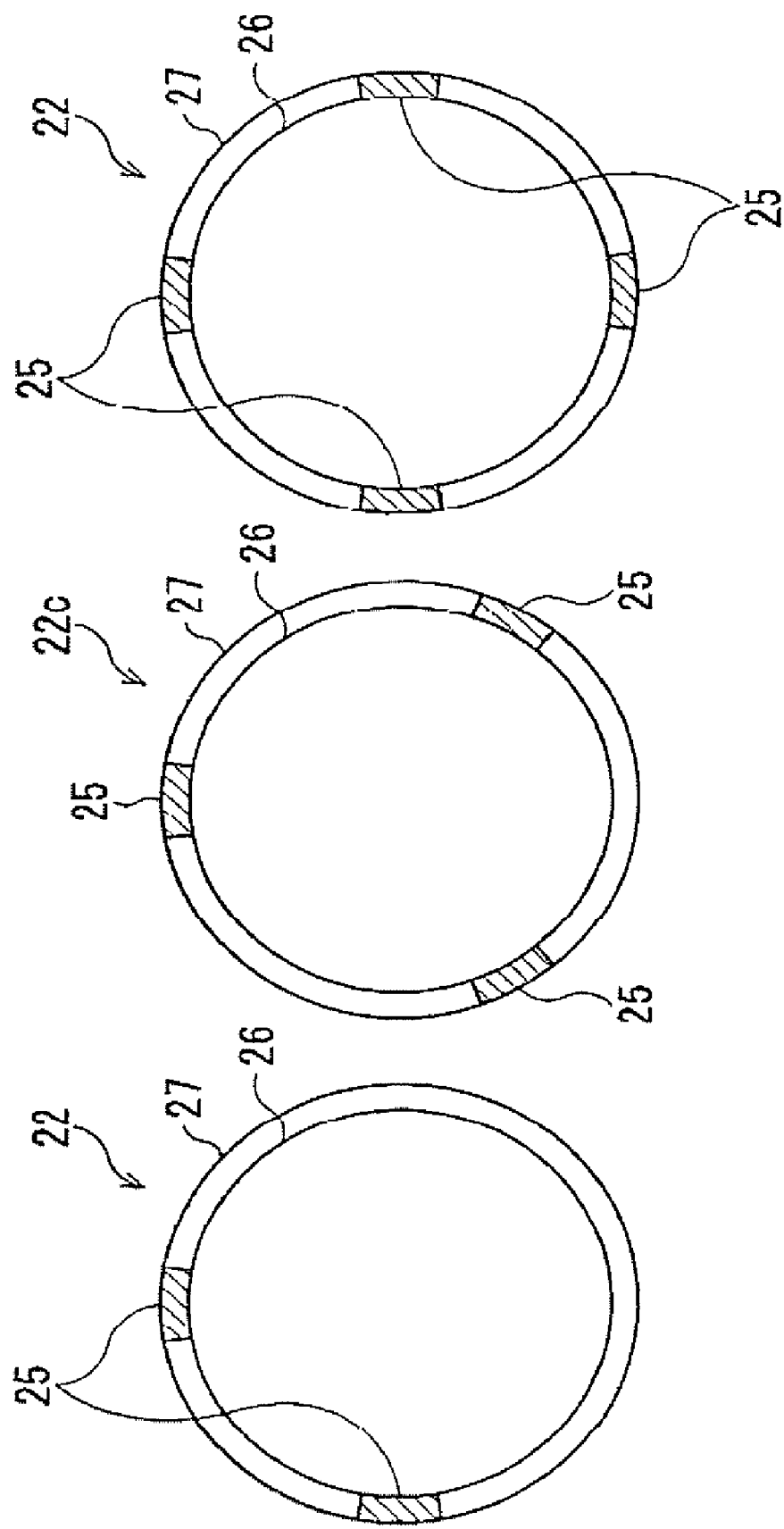

CONFIGURATION DETECTION DEVICE FOR ENDOSCOPE

BACKGROUND OF THE INVENTION

1. Field of the Invention

The present invention relates to a configuration detection device for detecting a configuration of an endoscope, especially for detecting a configuration of an endoscope that is inserted into a body for an observation.

2. Description of the Related Art

In a medical endoscopic observation, an endoscope must be inserted into a body in accordance with the shapes of body organs that are to be examined, because the end of the endoscope should not come into contact with them.

Therefore, an endoscope inspection system where a configuration of a scope inserted into a body is confirmed in an X-ray transmitted image generated by transmission of an X-ray to a subject, during an endoscopic observation, has been known. Further, a detection device for detecting a configuration of an inserted scope, where a configuration of a scope inside a body is detected by finding a change of a magnetic field, using a magnetic scope, has also been known.

On the other hand, an optical configuration detection device using a plurality of fiber bundles, where a light absorbing unit is provided for each fiber bundle, and where each of the fiber bundles is used for detecting a curvature of a subject in one direction, has also been known.

X-ray exposure may have negative effects on body health when the degree of exposure is over a permissible amount. On the other hand, if magnetism is used for detecting the configuration of an inserted scope, then if the subject is out of range of the magnetic field, the configuration may not be detected, or the accuracy of detection of the configuration may decrease.

When adopting an aforementioned optical configuration detector probe to detect a configuration of an inserted scope, the choice of endoscope to use with such an optical configuration detector probe is limited. The reason is that such an optical configuration detector probe requires a wide diameter, due to use of a plurality of optical fiber bundles. Further, in recent trends, the diameters of endoscopes have been narrowed, so as not to cause pain to a subject person; thus, the diameters of the associated forceps mouths have also been narrowed. Therefore, an optical configuration detector probe can not be adopted to detect a configuration of an inserted scope without narrowing the diameter thereof in order to adjust the diameter of the associated forceps mouth.

Further, if the number of fiber bundles included in such an optical configuration detector probe is decreased to narrow the diameter of the optical configuration detector probe, the precision of detection of the configuration of an inserted scope decreases.

SUMMARY OF THE INVENTION

Therefore, an objective of the present invention is to provide a configuration detection device for detecting a configuration of an endoscope with a narrow diameter but a high precision of detection.

The purpose of a configuration detection device, according to the present invention, is to detect a configuration of an endoscope. The configuration detection device includes a light-providing optical fiber, a light reflector, a curvature-detecting optical fiber, and a light modulator. The light-providing optical fiber transmits detection light in a plurality of wavelength ranges that have different wavelengths from one another. The light reflector reflects the detection light as reflected light, in the same reflection ratio as for the wavelength ranges, the light reflector being provided at the output end of the light-providing optical fiber. The curvature-detecting optical fiber transmits the reflected light, the curvature-detecting optical fiber being bent together with the endoscope. The light modulator modulates at least one of the strength or the wavelength of the reflected light for each of the wavelength ranges, the light modulator being provided in the curvature-detecting optical fiber. The configuration of the endoscope is detectable, based on at least one of the strength or the wavelength of the reflected light that is pre-modulated and post-modulated, and based on the distance between the light modulator and the output end of the curvature-detecting optical fiber.

The light modulator may absorb a part of the reflected light. A plurality of light modulators may be provided at equidistant positions from the output end of the curvature-detecting optical fiber.

The same number of light modulators may be provided in one of the curvature-detecting optical fibers as the number of wavelength ranges of the detection light.

The closer the light modulators are to the output end of the light-providing optical fiber, the shorter may be the distance between the light modulators.

A plurality of the curvature-detecting optical fibers may be arranged around the light-providing optical fiber.

The light modulator may modulate the reflected light so that the wavelength ranges that are modulated have different wavelengths from one another.

The configuration detection device may, further, include a light source that emits the detection light, and a light detector that detects at least one of the strength or the wavelength of each of the wavelength ranges that are modulated.

The purpose of a configuration detection system, according to the present invention, is to detect a configuration of an endoscope. The configuration detection system includes a light source, a fiber bundle, a light detector, a configuration detector, and an image display. The light source emits detection light containing a plurality of wavelength ranges that have different wavelengths from one another. The fiber bundle includes a light-providing optical fiber, a light reflector, a curvature-detecting optical fiber, and a light modulator. The light-providing optical fiber transmits the detection light. The light reflector reflects the detection light as reflected light, in the same reflection ratio as for the wavelength ranges, the light reflector being provided at the output end of the light-providing optical fiber. The curvature-detecting optical fiber transmits reflected light of the detection light, the curvature-detecting optical fiber being bent together with the endoscope. The light modulator modulates at least one of the strength or the wavelength of the reflected light for each of the wavelength ranges, the light modulator being provided in the curvature-detecting optical fiber. The light detector detects at least one of the strength or the wavelength of each or the wavelength ranges that are modulated. The configuration detector detects the configuration of the endoscope, based on the strength or the wavelength of the reflected light that is pre-modulated and post-modulated, and based on at least one of the distance between the light modulator and the output end of the curvature-detecting optical fiber. The image display displays an image representing the configuration of the endoscope that is detected.

BRIEF DESCRIPTION OF THE DRAWINGS

The present invention will be better understood from the description of the preferred embodiments of the invention set forth below, together with the accompanying drawings, in which:

FIG. 4 is a view representing light loss sections provided on a curvature-detecting optical fiber for detecting a curvature on the fiber bundle;

FIG. 22 is a graph representing the absorption of the reflected light that passes through the light loss section provided on a straight area or the fiber bundle in the second embodiment; and FIG. 23 is a view representing sections of the curvature-detecting optical fibers in an example and in the first and second embodiments.

DESCRIPTION OF THE PREFERRED EMBODIMENTS

Hereinafter, the preferred embodiments of the present invention are described with reference to the attached drawings.

Figure 1:
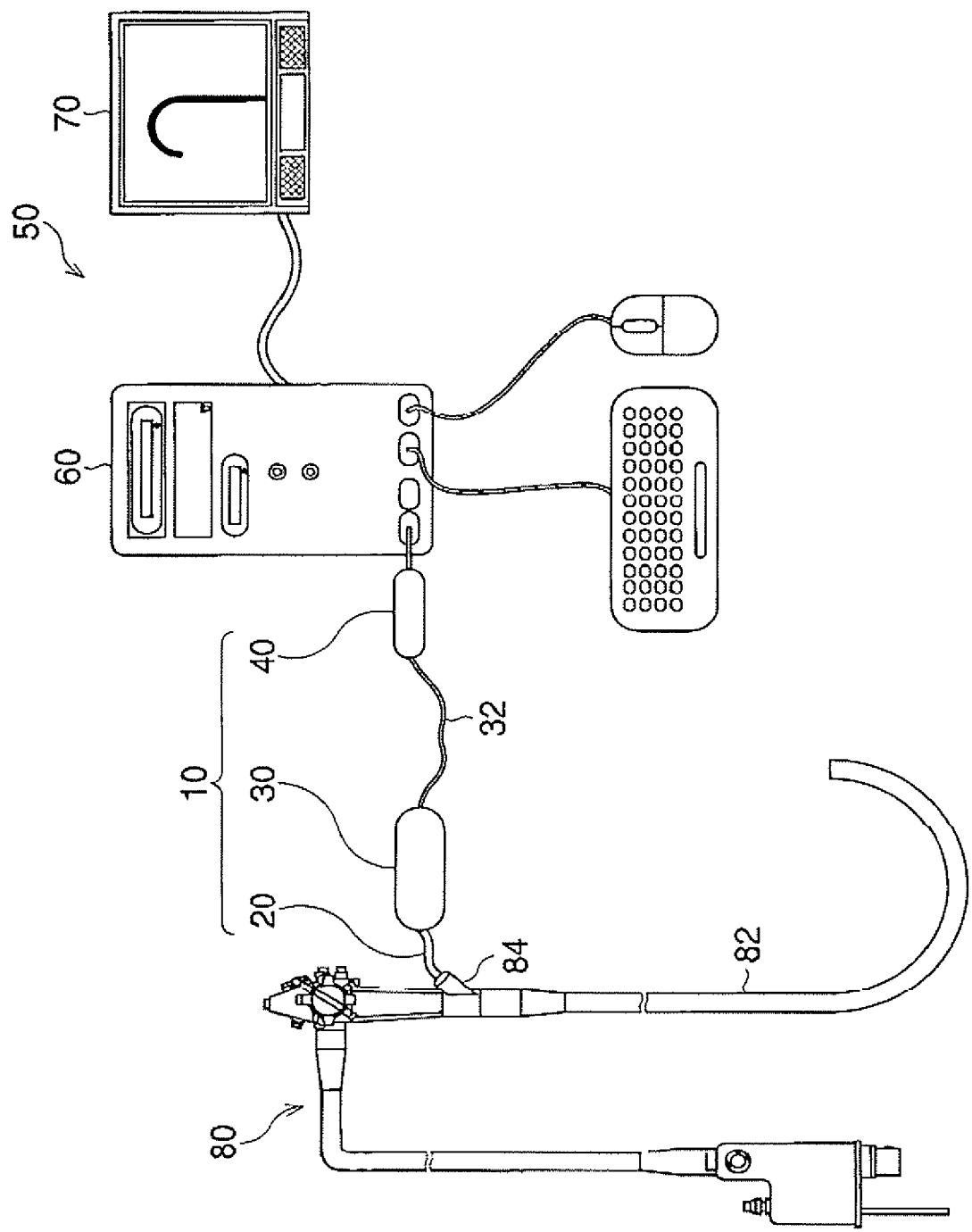
FIG. 1 is a view representing a configuration detection system of the first embodiment.
Figure 2:
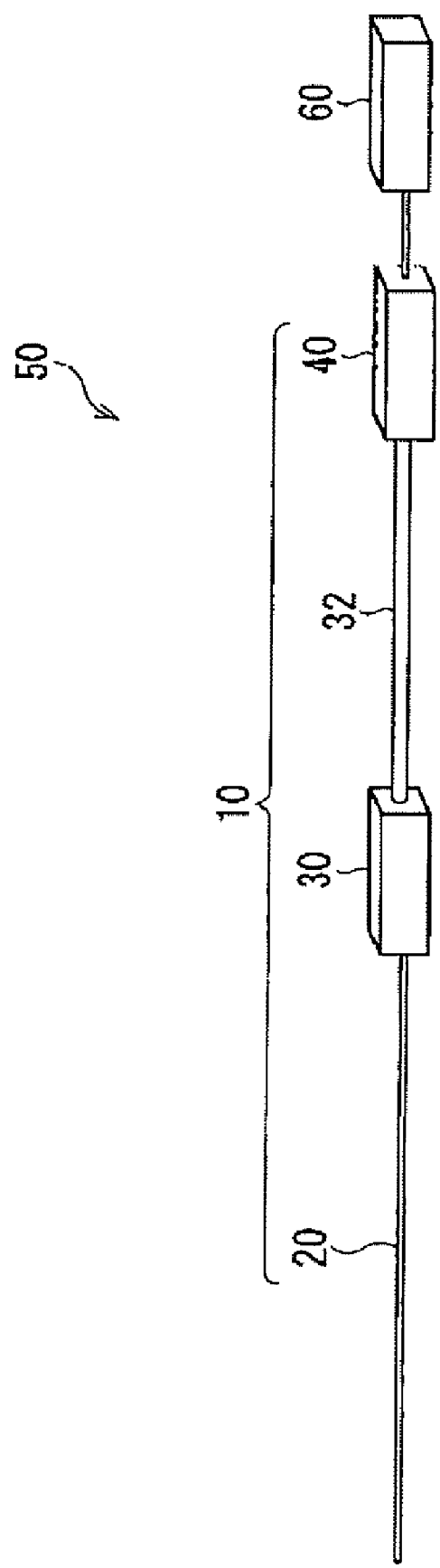
FIG. 2 is a view representing a configuration detector probe of the first embodiment.

As shown in FIGS. 1 and 2, in the configuration detection system 50 of the first embodiment, an endoscope detector probe 10, an image processing device 60, and a monitor 70 are provided. The endoscope detector probe 10 includes a fiber bundle 20, a light receiving module 30, and a connector 40, The fiber bundle 20 is connected to the light receiving module 30, and the light receiving module 30 is connected to the connector 40 via a cable 32.

The configuration detection system 50 is used for detecting a configuration of an insertion section 82 that is provided at the end of a scope 80, and that is inserted into a body of a subject person. That is, first, the fiber bundle 20 is inserted into the scope 80 through a forceps channel 84, to be flexible together with the insertion section 82. Signals representing the curvature of the fiber bundle 20 are transmitted to the image processing device 60. In the image processing device 60, the configuration of the fiber bundle 20 is detected based on the received signals, and then an image representing the detected configuration of the fiber bundle 20 is generated. The image representing the configuration of the fiber bundle 20 is displayed on the monitor 70, as exemplified in FIG. 1.

When the configuration of the fiber bundle 20 is detected, the configuration of the insertion section 82 that is flexible together with the fiber bundle 20 is also detected. As explained above, in the configuration detection system 50, the configuration of the insertion section 82 is detected based on the curvature of the fiber bundle 20. To detect the configuration of the insertion section 82 in this manner, the fiber bundle 20 is designed to have a plurality of detection points, where the curvatures thereof are able to be detected. The means of detecting the curvature and configuration of the fiber bundle 20 are explained below.

Figure 3:
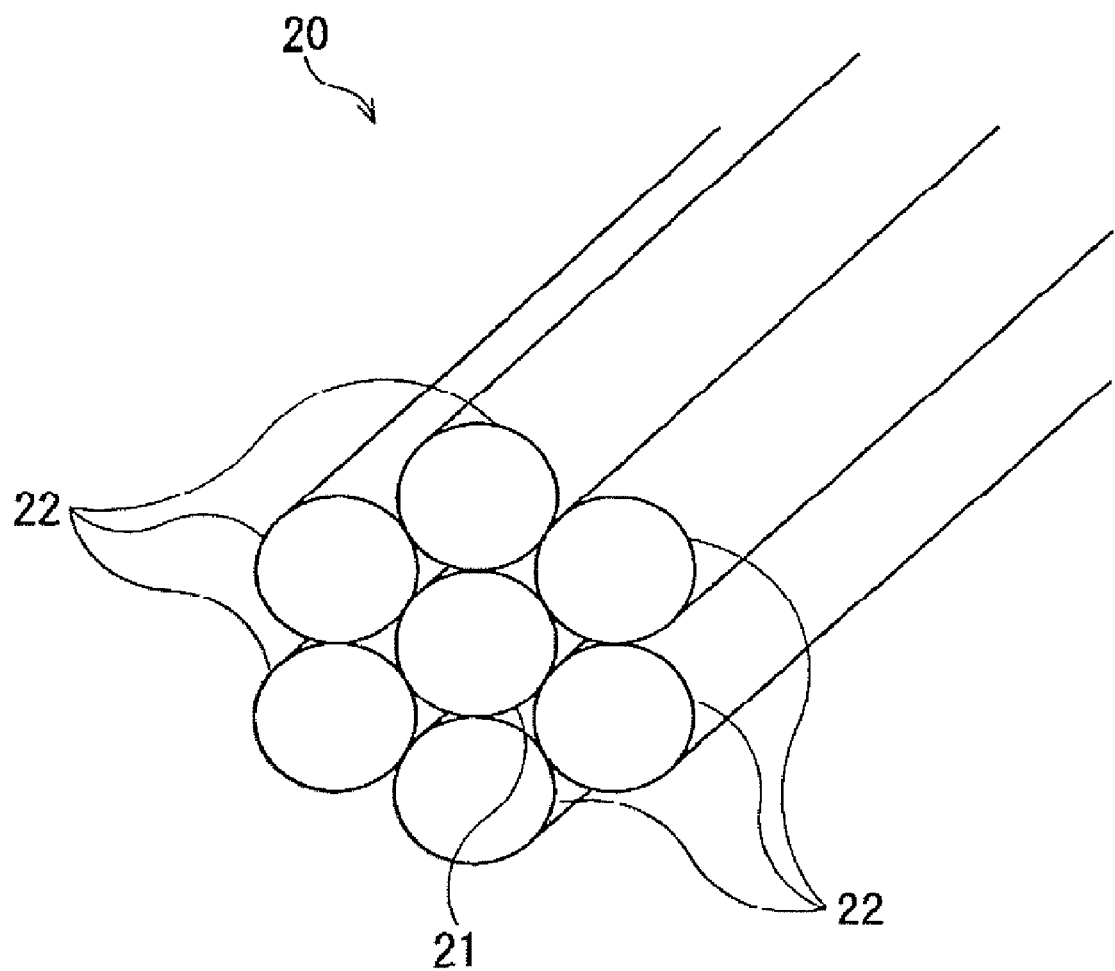
FIG. 3 is a perspective view representing a fiber bundle.

In the fiber bundle 20, as represented in FIG. 3, a light-providing optical fiber 21 and a plurality of curvature-detecting optical fibers 22 that are bent together with the insertion section 82, and that are in contact with each other in parallel, are provided. In the light-providing optical fiber 21 and curvature-detecting optical fibers 22, a core is provided in the center area, and a clad is coated around the core (both not shown). Therefore, in the light-providing optical fiber 21 and curvature-detecting optical fibers 22, the light is transmitted from the input end to the output end thereof, without any substantial loss caused by total internal reflection of the light at the border of the core and clad inside thereof.

Detection light for detecting the curvature of the fiber bundle 20, emitted by a light source (not shown) provided in the connector 40, enters the light-providing optical fiber 21. The detection light is transmitted to the end of the fiber bundle 20 by the light-providing optical fiber 21. At the end of the fiber bundle 20 (that is, at the output end of the light-providing optical fiber 21), a mirror (not shown) is provided. Reflected light of the detection light, which is reflected by the mirror, enters the curvature-detecting optical fibers 22. Then, the reflected light is received by a light-receiving element provided in the light receiving module 30.

As shown in FIG. 4, on the surfaces of the all of the curvature-detecting optical fibers 22, a plurality of light loss sections 25 that absorb a part of the reflected light are provided. The amount of the reflected light absorbed by the light loss sections 25 varies in accordance with the curvature of the positions of the fiber bundle 20 where the light loss sections 25 are provided, as explained below. Therefore, the curvature of the fiber bundle 20 is calculated based on the strength of the reflected light before and after passing through the light loss sections 25.

To simplify the calculation of the curvature, the light loss sections 25, for example, are provided as follows. One of a pair of light loss sections 25 is provided on a line parallel to an X-axis of a coordinate system that is on a surface perpendicular to the fiber bundle 20 in the straight state, and which has the origin O in the center of the fiber bundle 20. The other of a pair of the light loss sections 25 is provided on a Y-axis of the aforementioned coordinate system (see the sections of the fiber bundle 20 represented in FIG. 4, taken along lines I-I and II-II).

Figure 5:
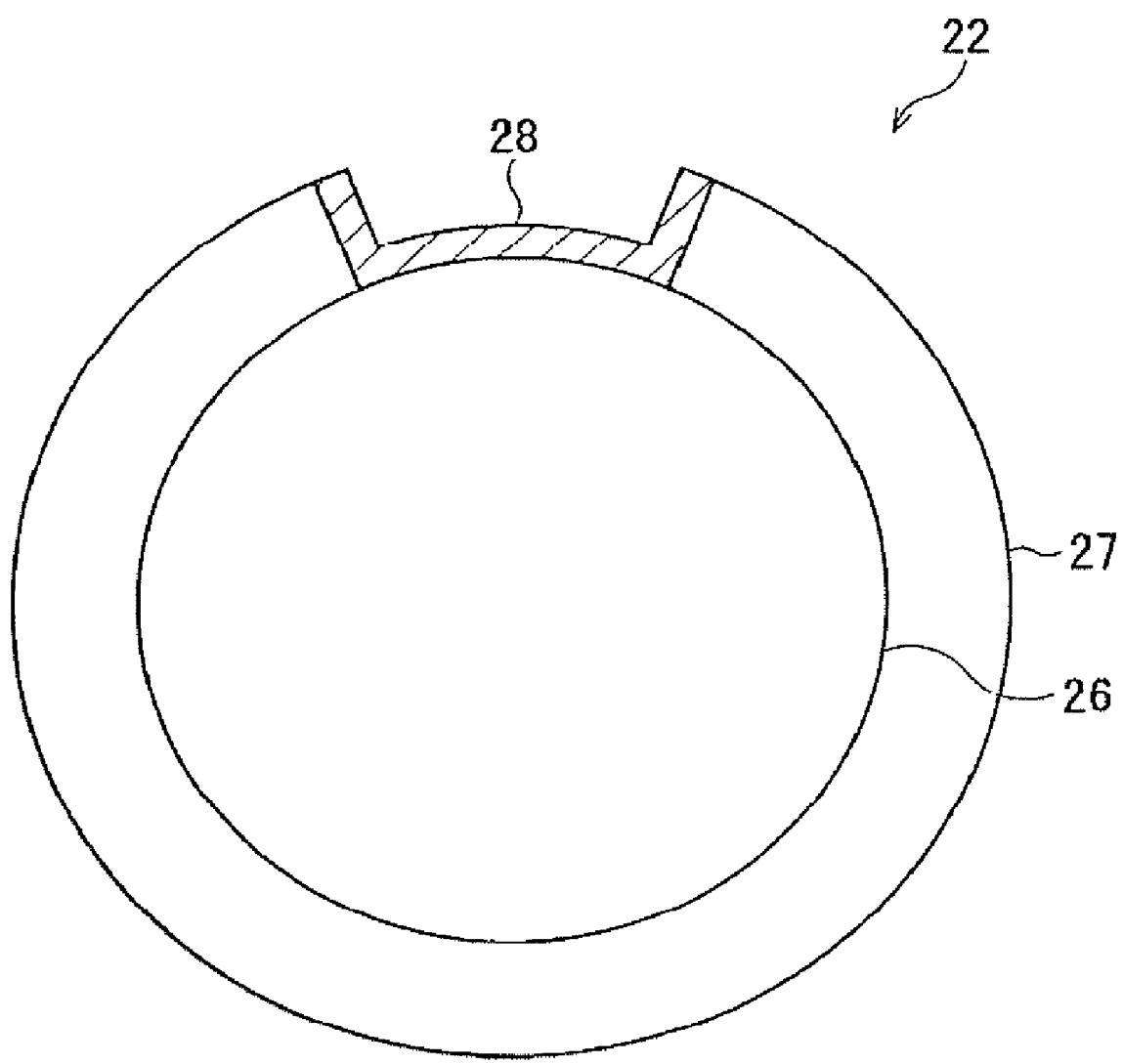
FIG. 5 is a sectional view or the curvature-detecting optical fiber at the light loss section, taken along a perpendicular direction to the longitudinal direction thereof.

The process for forming the light loss sections 25 is explained below. First, a part of the clad 27 is cut off (see FIG. 5). Then, a coating material 28 that absorbs a component off light having a predetermined wavelength is coated on the surface of the core 26 where a part of the clad 27 is cut away. An adhesive used for adhesion of the fiber bundle 20 to a sheath (not shown) is deposited on the coating material 28, and thus the light loss sections 25 are formed.

A part of the reflected light of the detection light, which is transmitted inside the core 26 in the curvature-detecting optical fibers 22, including the light loss sections 25 formed by the above means, enters the layer of the coating material 28, via total internal reflection. At that time, a part of the wavelength range of the reflected light is absorbed by the light loss section 25, and then, the other wavelength range of the reflected light is output from the curvature-detecting optical fibers 22.

Figure 6:
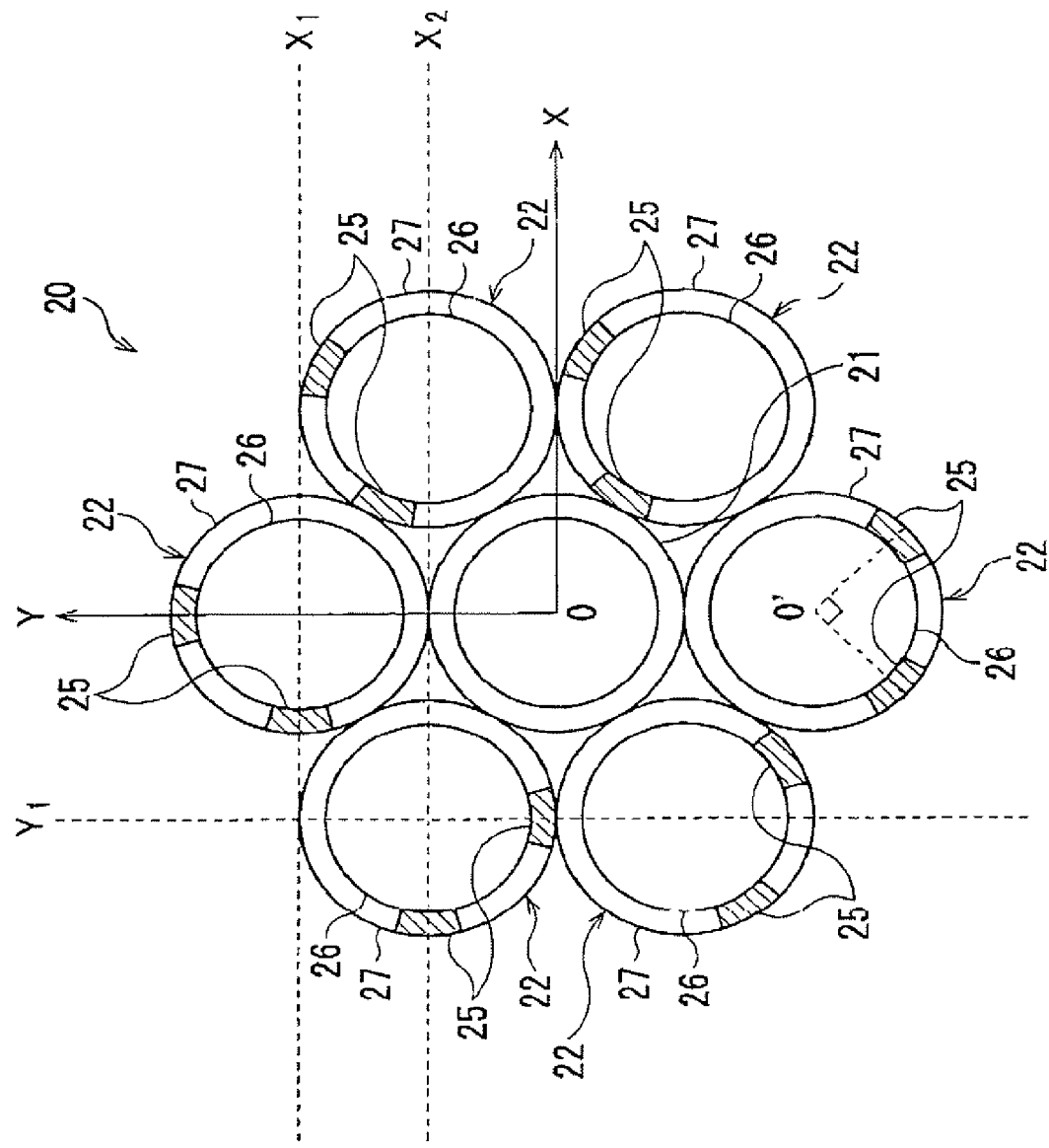
FIG. 6 is a sectional view of the fiber bundle of the first embodiment at the light loss section, taken along a perpendicular direction to the longitudinal direction thereof.

The light loss sections 25 are preferably provided on lines parallel to the X-axis in the aforementioned coordinate system (for example, lines $X_1$ and $X_2$, represented in FIG. 6) and on lines parallel to the Y-axis (for example, lines $Y_1$ and the Y-axis itself) However, the arrangement of the light loss sections 25 is not limited to those, as can be seen from some curvature-detecting optical fibers 22, represented in FIG. 6.

In a case where the light loss sections 25 are not provided on lines parallel to the X-axis and Y-axis, the light loss sections 25 are more advantageously provided to describe a right angle by the two light lose sections 25 and the center point O' of the curvature-detecting optical fibers 22, as represented in FIG. 6, to simplify the calculation of the curvature, as explained below.

Note that all of the light loss sections 25 are described to be on the same section in FIG. 6; that is, all of the light loss sections 25 are described to be located at equidistant points from the end of the fiber bundle 20, for convenience of explanation; however, the light loss sections 25 are actually arranged in various positions on the fiber bundle 20 (see FIG. 4 and other relate figures).

Figure 7:
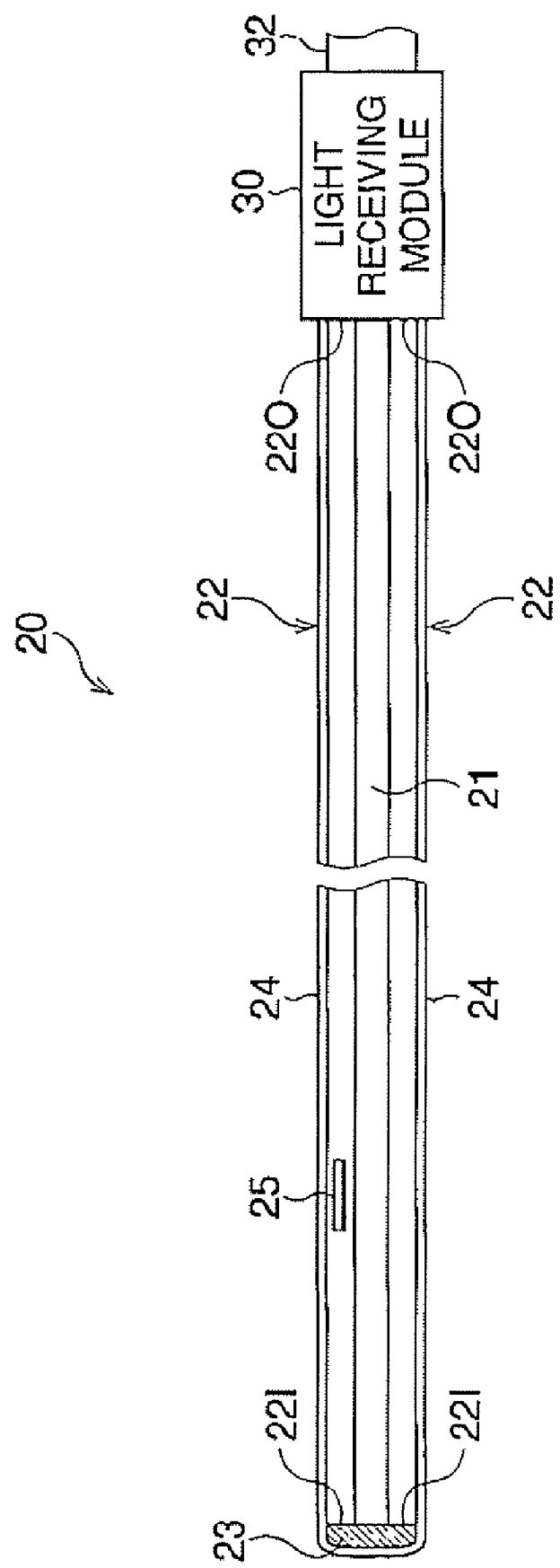
FIG. 7 is a sectional view of the fiber bundle taken along a surface that runs through the center of the fiber bundle and that extends in a longitudinal direction thereof.

As shown in FIG. 7, the surface of the fiber bundle 20, that is, the outside of the curvature-detecting optical fibers 22, is covered by the sheath 24. The sheath 24 covers the entire surface of the fiber bundle 20, including the end of the fiber bundle 20 where the mirror 23 is provided, so that leakage of the detection light and the reflected light thereof are prevented.

The curvature-detecting optical fibers 22 adhered to the sheath 24 at the light loss sections 25 au explained above. In addition to this, at the output end 22O on the module 30 side, and at the input end 22I on the mirror 23 side, the curvature-detecting optical fibers 22 adhere to the sheath 24. Thus, all of the curvature-detecting optical fibers 22 are connected to the light-providing optical fiber 21 (see FIGS. 3 and 6). Therefore, the light-providing optical fiber 21 and the curvature-detecting optical fibers 22 are bent together with one another.

Note that, in terms of the reflection of the detection light by the mirror 23, providing a light emission area where the detection light enters into the center of the mirror 23, then diffusing the reflected light around the light emission area, and finally causing the reflected light to enter each of the curvature-detecting optical fibers 22 evenly, is easier than the opposite thereof; that is, than providing a light emission area at the periphery of the mirror 23, and diffusing the reflected light towards the center of the mirror 23 evenly. Therefore, the curvature-detecting optical fibers 22 are arranged around the light-providing optical fiber 21 (see FIGS. 3 and 6).

Figure 8:
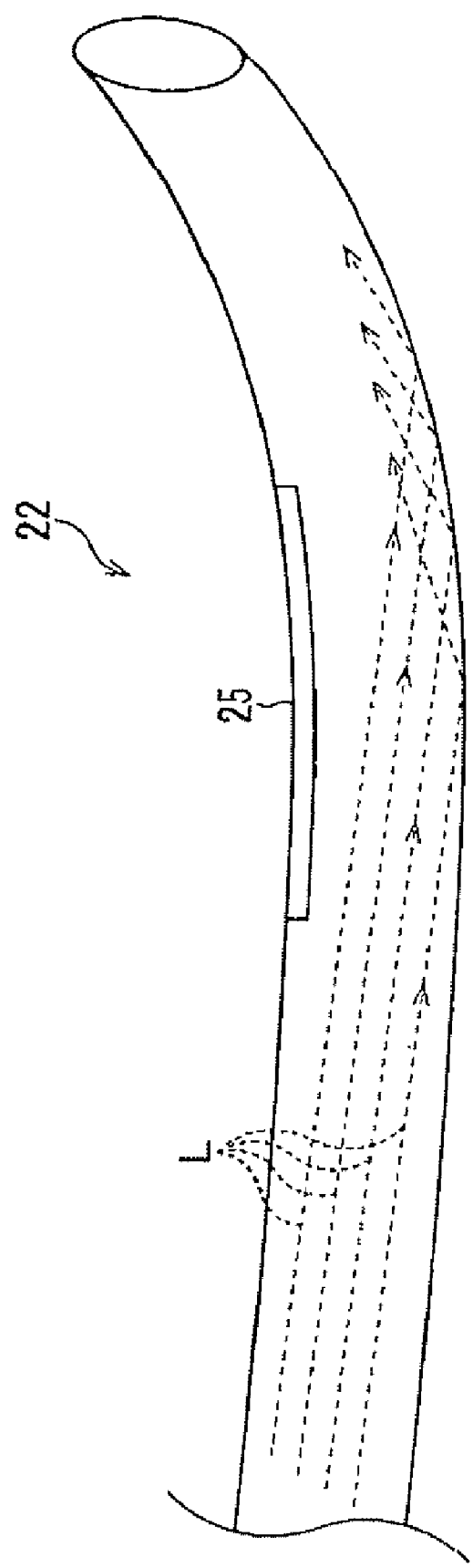
FIG. 8 is a side view representing the curvature-detecting optical fiber, which is bent so that a small amount of the reflected light enters the light loss section.

When the detection light enters the light-providing optical fiber 21 from the light receiving module 30 side and the detection light is reflected by the mirror 23, the reflected light L enters the input ends 22I of the curvature-detecting optical fibers 22 (see FIG. 7). At that time, for example, the light loss section 25 is provided on the upper side or the curvature-detecting optical fiber 22, and the curvature-detecting optical fiber 22 is bent where the light loss section 25 is at the bottom of the curved curvature-detecting optical fibers 22, so that the reflected light L hardly enters the light loss sections 25, as represented in FIG. 8.

Figure 9:
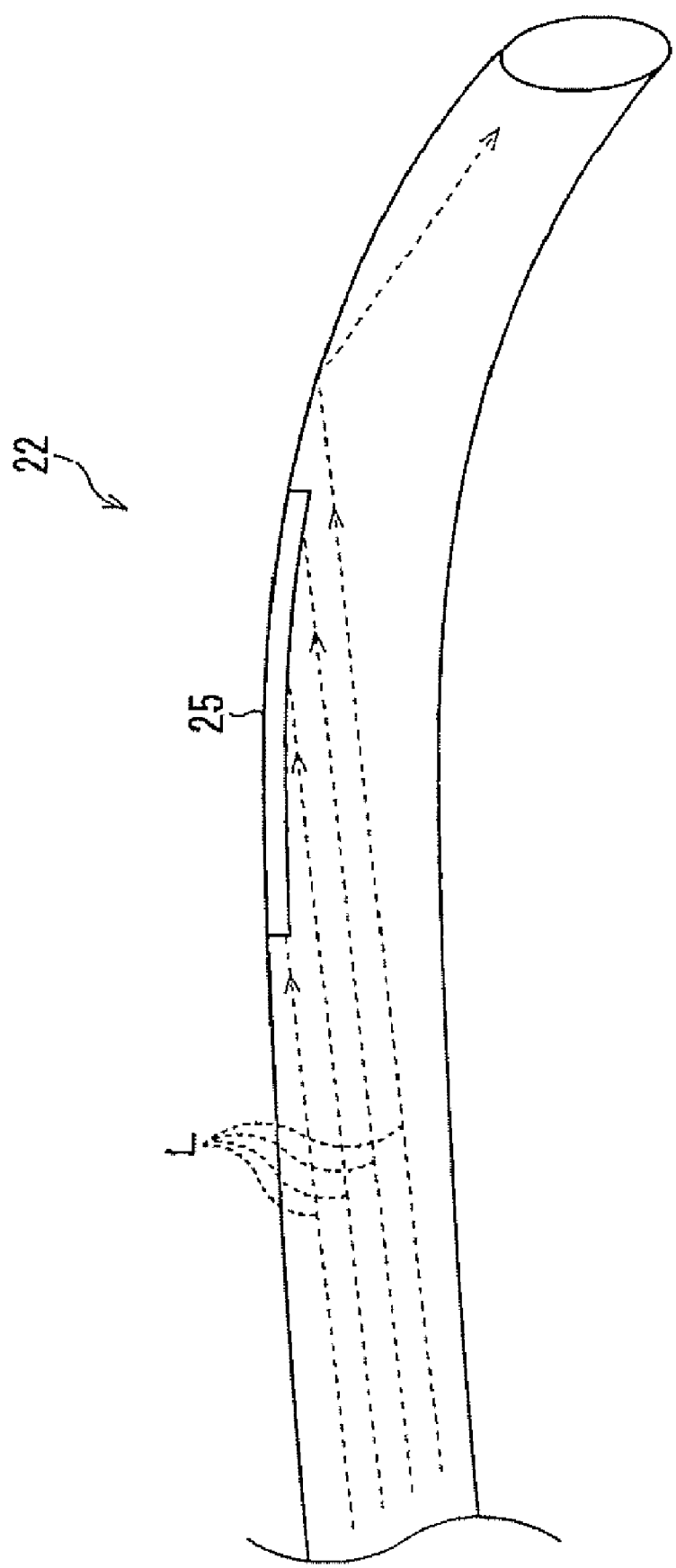
FIG. 9 is a side view representing the curvature-detecting optical fiber, which is bent so that a large amount of the reflected light enters the light loss section.

On the other hand, as represented in FIG. 9, when the light loss sections 25 is provided on the upper side of the curvature detecting optical fiber 22, and the curvature-detecting optical fibers 22 is bent where the light loss sections 25 is on the top of the curved curvature-detecting optical fibers 22, most of the reflected light L enters the light loss sections 25. As is clear from the explanation above, the curvature of the curvature-detecting optical fibers 22 at the position where the light loss sections 25 are provided (that is, the curvature of the fiber bundle 20) can be calculated by detecting the strength of the reflected light L after it passes through the light loss sections 25.

Figure 10:
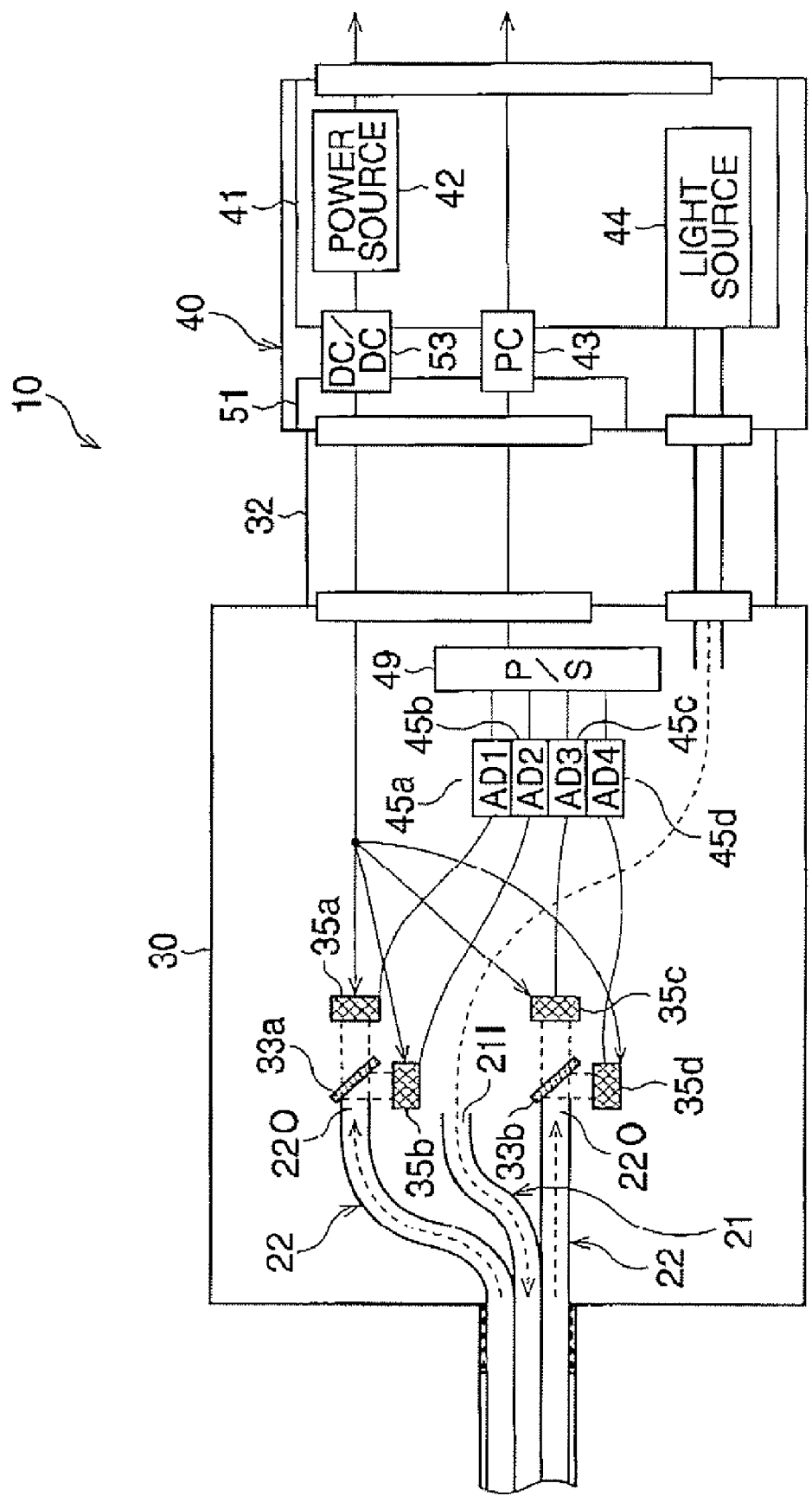
FIG. 10 is a block diagram of a module and a connector of the first embodiment.

A general circuit 41 is provided in the connector 40 (see FIG. 10). In the general circuit 41, a power source 42 and a light source 44 are provided. When the connector 40 is connected to the image processing device 60 (see FIGS. 1 and 2), electric power is supplied to the power source 42 via the image processing device 60, then electric power is further supplied to the light source 44 from the power source 42. The light source 44 to which electric power is supplied emits a laser beam that includes two components of different wavelengths from each other as the detection light.

The emitted detection light enters the input end 21I of the light-providing optical fiber 21. Then, the detection light is reflected by the mirror 23, and the reflected light enters the curvature-detecting optical fibers 22. The reflected light L of the detection light is transmitted by the curvature-detecting optical fibers 22, and then is output from the output ends 22O of the curvature-detecting optical fibers 22. The mirror 23 reflects wavelength ranges of the detection light that are different from one another in the same reflection ratio.

Each of the reflected lights L that is output from the two output ends 22O is decomposed into two wavelength ranges by first and second dichroic mirrors 33a and 33b, then the wavelength ranges are received by the first to fourth light-receiving elements 35a to 35d. Note that, in practice, as shown in FIGS. 3 and 6, six curvature-detecting optical fibers 22 are provided in the fiber bundle 20, although only two curvature-detecting optical fibers 22 are represented in FIG. 10, for simplification thereof. The numbers of the dichroic mirrors, light-receiving elements, and A/D converters explained below are adjusted in accordance with the number of the curvature-detecting optical fibers 22.

In the connector 40, a patient circuit 51 and a DC/DC converter 53 are provided. The DC/DC converter is connected to the general circuit 41 and the patient circuit 51. The DC/DC converter is an insulation type DC/DC converter, and causes the patient circuit 51 to generate electric power based on electric power supplied to the general circuit 41, while maintaining an insulated state from the general circuit 41 and the patient circuit 51. The first to fourth light-receiving elements 35a to 35d are driven by supplying electric power that is generated by the patient circuit 51. Note that the amount of electric power generated by the patient circuit 51 is controlled to be lower than the amount of electric power supplied to the general circuit 41, for safety reasons.

The first to fourth light-receiving elements 35a to 35d are photodiodes, and detect the amount of the received light. When the first to fourth light-receiving elements 35a to 35d receive the wavelength range of the reflected light, electric signals in accordance with each amount of the received wavelength range are output as curvature signals. The curvature signals generated by the first to fourth light-receiving elements 35a to 35d, are transmitted to first to fourth A/D converters 45a to 45d, respectively. Each of the curvature signals is converted from analog to digital by the first to fourth A/D converters 45a to 45d, respectively.

The digitized curvature signals are transmitted to a parallel-serial conversion circuit 49. The curvature signals are converted from the parallel signals to the serial signals by the parallel-serial conversion circuit 49. The serialized curvature signals are transmitted to a photo-coupler (PC) 43. The curvature signals are transmitted to the general circuit 41 by the photo-coupler 43, and then are further transmitted to the image processing device 60.

In the processing device 60, the curvature of the fiber bundle 20 at each of the light loss sections 25 is calculated based on the curvature signals for each of the wavelength ranges of the reflected light L. Note that a pair of the light loss sections 25 are provided in one curvature-detecting optical fiber 22, and the wavelengths of light that are absorbed by the coating materials 28 coated on each of the light loss sections 25 are different from each other, so as to be identical to the wavelengths of the two ranges of the used detection light. Therefore, the curvature of the curvature-detecting optical fiber 22 is calculated for each pair of the light loss sections 25 by the image processing device 60.

Further, in the image processing device 60, information representing distances between each of the light loss sections 25 and the output end 22O of the curvature-detecting optical fiber 22 is previously stored. Therefore, the configuration of the fiber bundle 20 at the time of use is detected by the image processing device 60, based on the positions of the light loss sections 25, and based on the curvatures in the X-axis direction and the Y-axis direction of the fiber bundle 20 at the positions where the light loss sections 25 are provided. Then, image signals representing the detected configuration of the fiber bundle 20 are transmitted from the image processing device 60 to the monitor 70. As a result, the configuration of the fiber bundle 20 (that is, the configuration of the insertion section 82 of the scope 80) is displayed on the monitor 70 (see FIG. 1).

Note that the output ends 22O of the curvature-detecting optical fibers 22 are represented as being in contact with a surface of the light receiving module 30 in FIG. 7; however, in practice, the output ends 22O are inside the light receiving module 30. Further, the distances between the surface of the light receiving module 30 and the two output ends 22O are represented as different from each other in FIG. 10; however, these distances are in fact equal, and the lengths of a plurality of the curvature-detecting optical fibers 22 are equal to one another.

Figure 11:
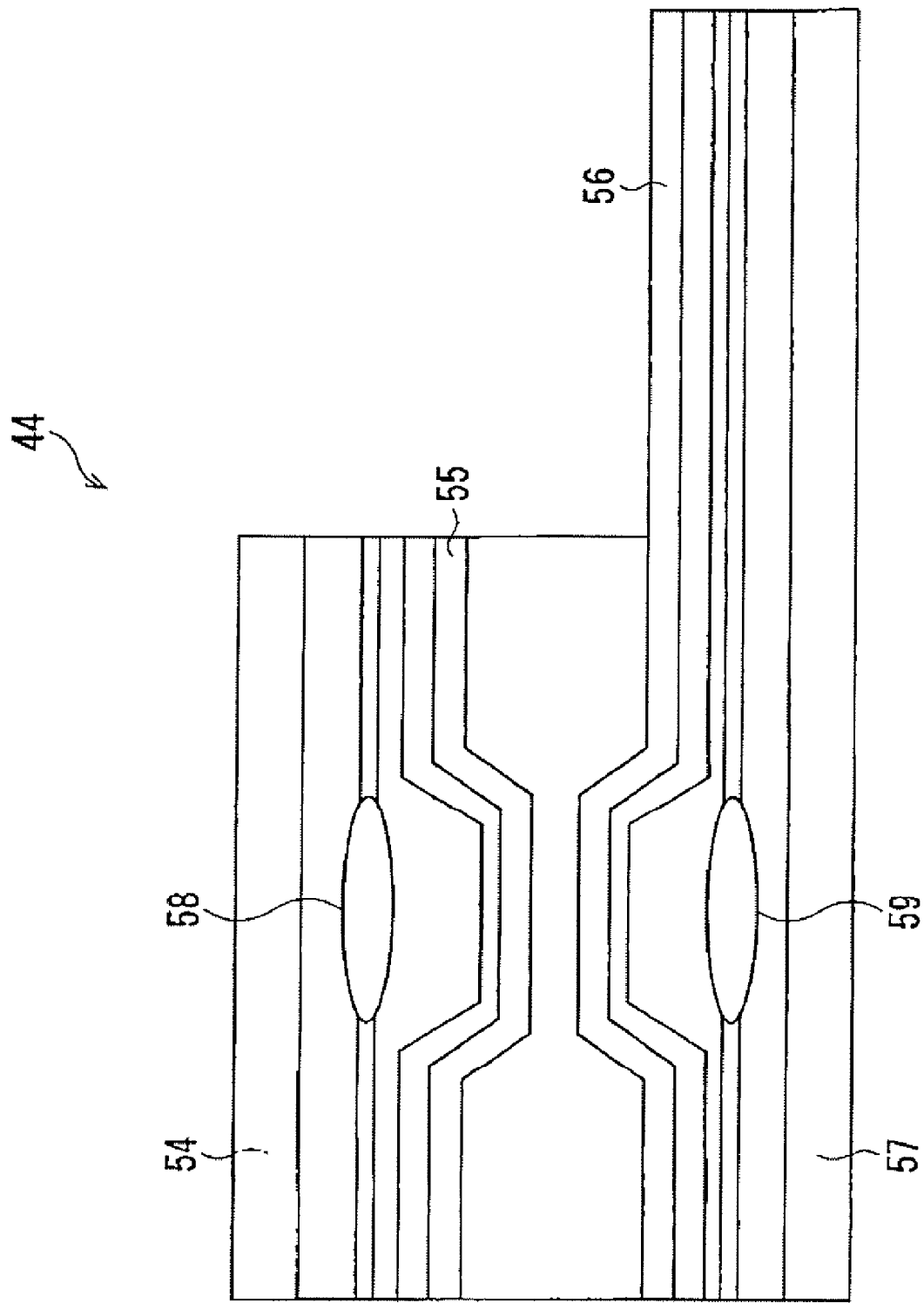
FIG. 11 is a view representing a light emission surface of a light source provided in the connector.
Figure 12:
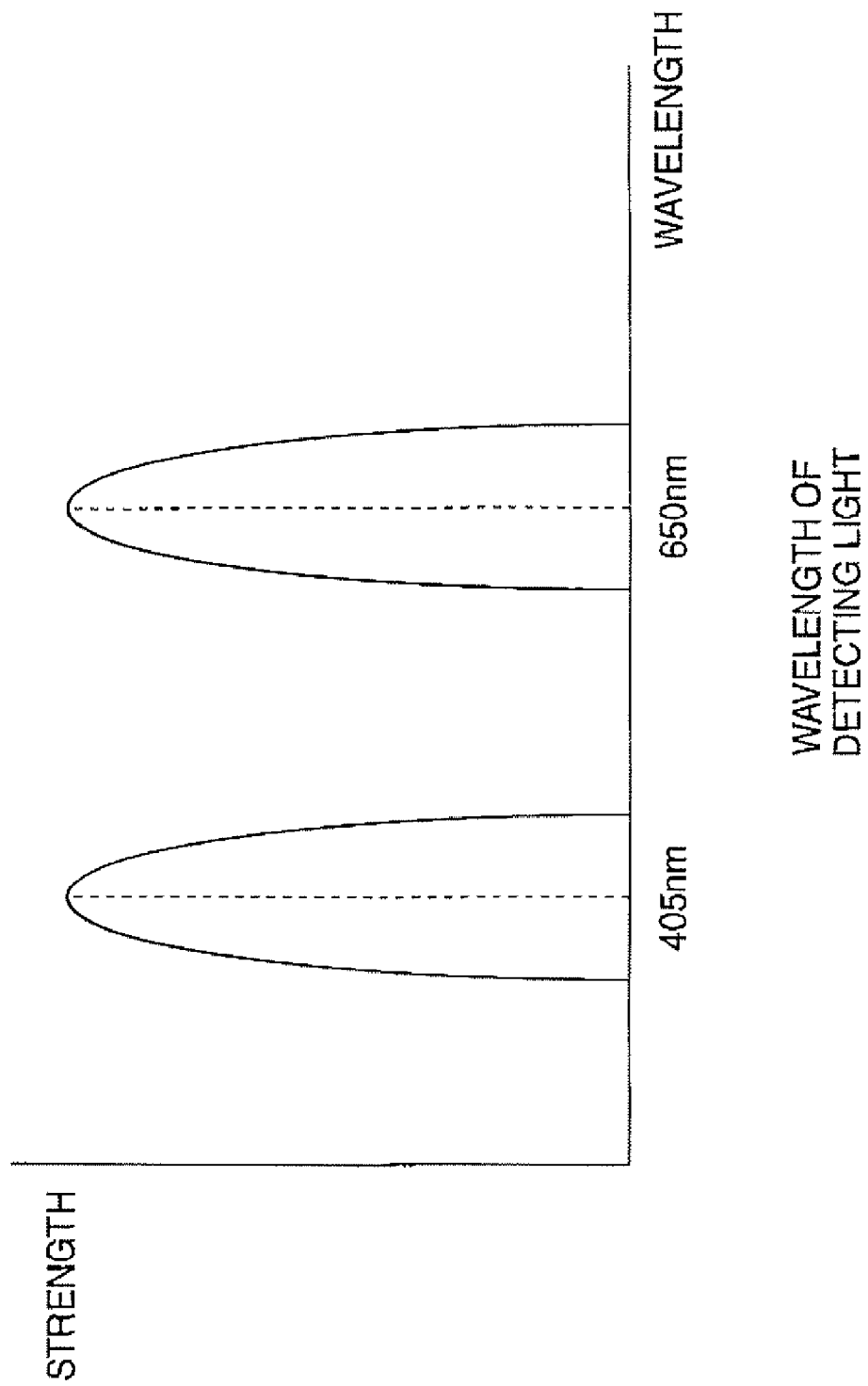
FIG. 12 is a view representing the wavelength and strength of detection light that is emitted by the light source of the first embodiment.

As shown in FIG. 11, in the light source 44, first to fourth electrodes 54 to 57, and first and second light emission sections 58 and 59, are provided. A first laser beam having a predetermined wavelength, as one of the components of the detection light, is emitted by the first light emission section 58, in a direction perpendicular to the paper of FIG. 11, when electric power is supplied to the first light emission section 58 by the first and second electrodes 54 and 55. Similarly to with the first laser beam, a second laser beam having a different wavelength from the first laser beam, as another component of the detection light, is emitted by the second light emission section 59, when electric power is supplied to the second light emission section 59 by the third and fourth electrodes 56 and 57. Note that as shown in FIG. 12, the wavelength of the first laser beam is 405 nm, and the wavelength of the second laser beam is 650 nm, and that these two wavelength ranges are independent; that is, these wavelength ranges do not overlap.

The absorption of the reflected light L of the detection light emitted by the light source 44 is explained below, as exemplifying first and second curvature-detecting optical fibers 22a and 22b (see FIG. 13). In the first curvature detecting optical fiber 22a, first and second light loss sections 25a and 25b are provided, and in the second curvature-detecting optical fiber 22b, third and fourth light loss sections 25c and 25d are provided, respectively. The first and third light loss sections 25a and 25c selectively absorb only the wavelength range centered on 405 nm of the first laser beam, and the second and fourth light loss sections 25b and 25d selectively absorb only the wavelength range centered on 650 nm of the second laser beam.

When the detection light containing the wavelength ranges of the first and second laser beam is reflected by the mirror 23, first and second reflected lights $L_1$ and $L_2$, which contain the same wavelength ranges including the first and second laser beams in the same ratio, and which have the same strength, enter the first curvature-detecting optical fiber 22a and the second curvature-detecting optical fiber 22b, respectively. The absorption of the first reflected light $L_1$ in the first curvature-detecting optical fiber 22a is explained below, with reference to FIGS. 13 and 14.

The first curvature-detecting optical fiber 22a is not bent, but is straight where the first light loss section 25a is provided. Therefore, the wavelength range centering on 405 nm contained in the first reflected light $L_1$ does not enter the first light loss section 25a, so that the strength of the wavelength range centering on 405 nm is maintained at the same level as when the first reflected light $L_1$ enters the first curvature-detecting optical fiber 22a from the mirror 23.

Next, the first curvature-detecting optical fiber 22a is bent where the second light loss section 25b is provided. However, the direction of the curvature where the second light loss section 25b is provided is different from the direction of the curvature that is the subject of the detection by the second light loss section 25b, so that the wavelength range centering on 650 nm is not absorbed by the second light loss section 25b. That is, for example, the second light loss section 25b is for detecting the curvature of the X-axis direction in the aforementioned coordinate system (see FIG. 6); on the other hand, the curvature-detecting optical fiber 22a is bent only in the direction parallel to the Y-axis direction in the coordinate system.

Next, the absorption of the second reflected light $L_2$ in the second curvature-detecting optical fiber 22b is explained below, with reference to FIGS. 13 and 15. The second curvature-detecting optical fiber 22b is not bent where the third light loss section 25c is provided. Therefore, the wavelength range centering on 405 nm contained in the second reflected light $L_2$, does not enter the third light loss section 25c, so that the strength of the wavelength range centering on 405 nm is maintained to be at the same level as when the second reflected light $L_2$ enters the second curvature-detecting optical fiber 22b from the mirror 23.

On the other hand, the second curvature-detecting optical fiber 22b is bent where the fourth light loss section 25d is provided. The direction of the curvature where the fourth light loss section 25d is provided is the same as the direction of the curvature that is the subject of the fourth light loss section 25d. Therefore, the wavelength range centering on 650 nm is absorbed by the fourth light loss section 25d, so that the amount of the absorbed wavelength range is proportioned to the angle of curvature of the second curvature-detecting optical fiber 22b.

Figure 13:
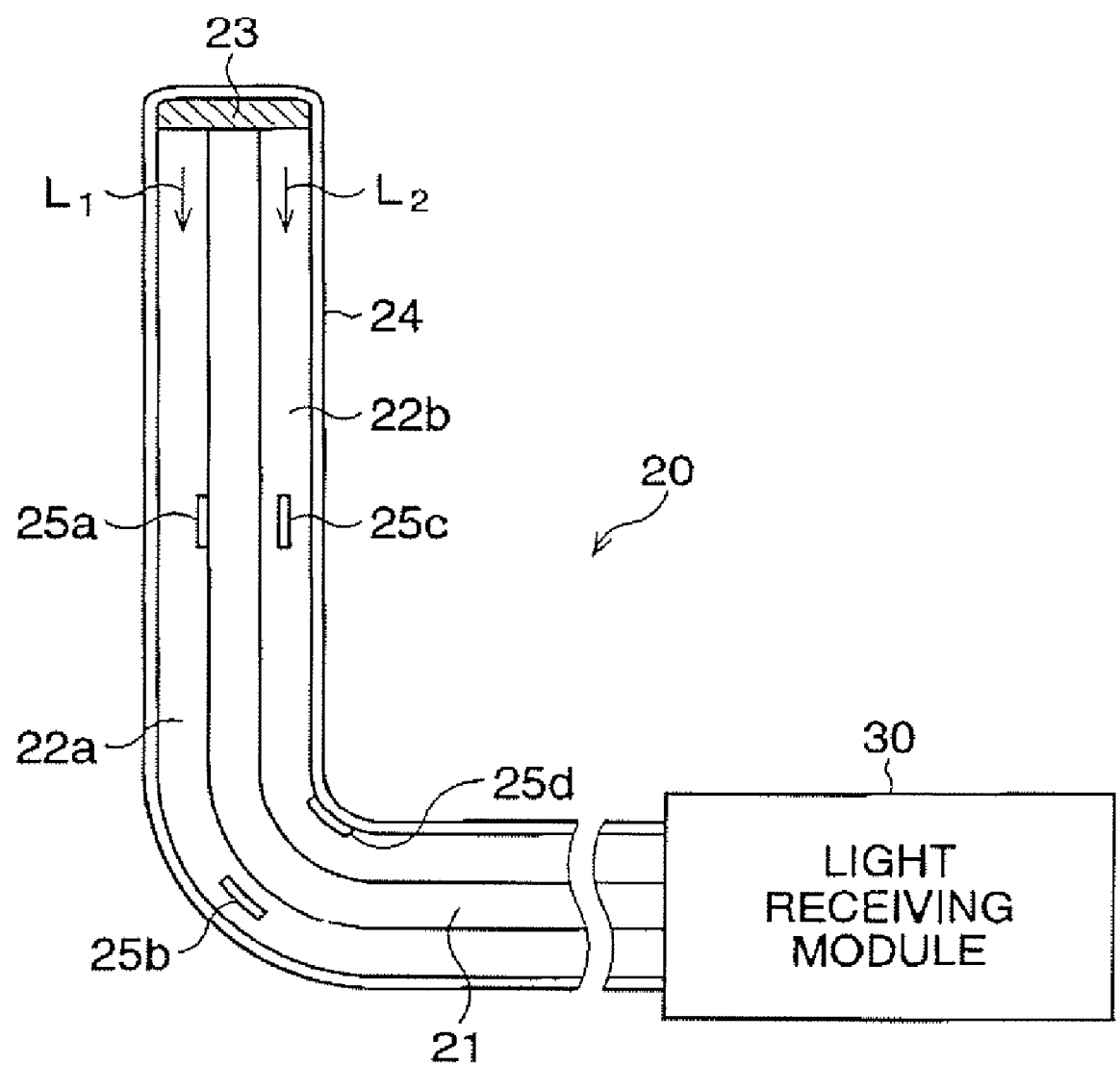
FIG. 13 is a sectional view of the fiber bundle of the first embodiment that is in the bent state, taken along a surface that runs through the center of the fiber bundle, and that extends in a longitudinal direction of the fiber bundle.
Figure 14:
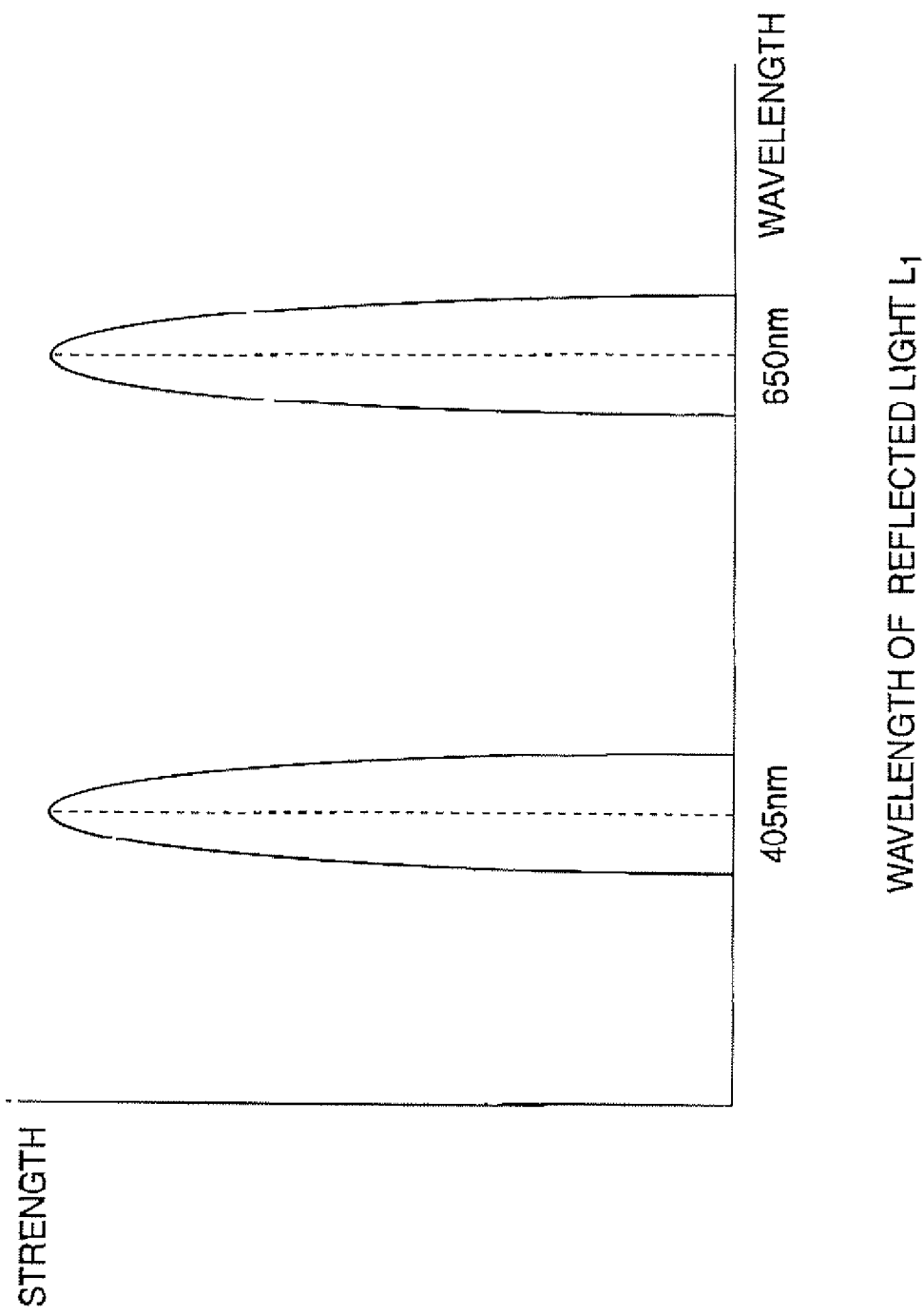
FIG. 14 is a graph representing the absorption of the reflected light that passes through the light loss section provided on a straight area of the fiber bundle in the first embodiment.
Figure 15:
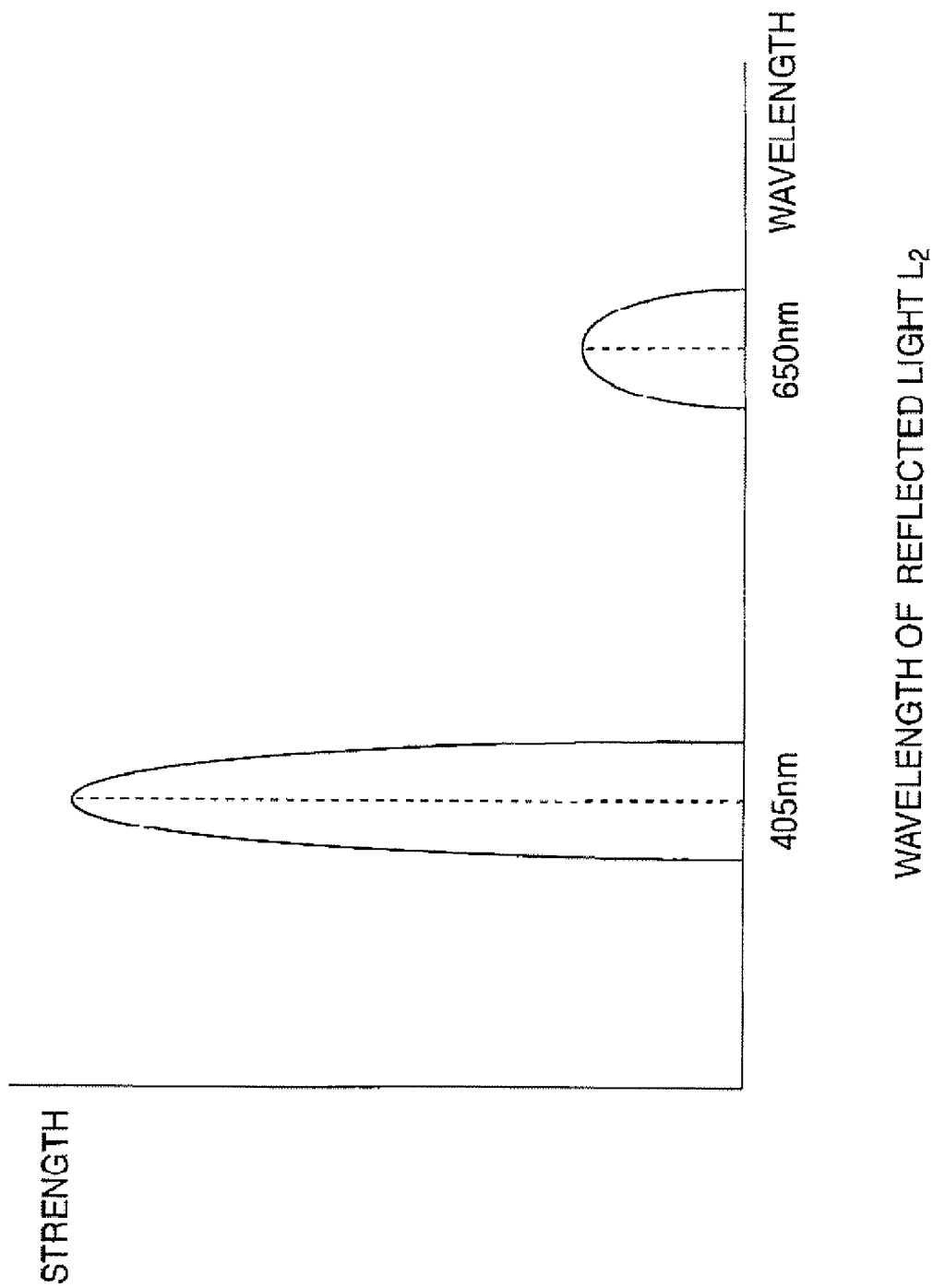
FIG. 15 is a graph representing the absorption of the reflected light that passes through the light loss section provided on a bent area of the fiber bundle in the first embodiment.

In FIGS. 13 to 15, for convenience of explanation, the curvature-detecting optical fiber 22 is bent only in the direction that is the subject of detection of the curvature by the light loss sections 25a to 25d, or is bent only in the direction that is not the subject of detection of the curvature by the light loss sections 25a to 25d. However, the curvature at a position of the curvature-detecting optical fiber 22 generally includes both components of the X-axis direction and the Y-axis direction. Therefore, the curvature of the curvature-detecting optical fiber 22 is calculated by putting together the detection results of the curvature in two directions, such as the X-axis direction and the Y-axis direction, as explained below.

As explained, calculating the curvature in two directions for one position of the curvature-detecting optical fiber 22 is required. Therefore, a pair of the light loss sections 25 are provided at the same position in the curvature-detecting optical fiber 22; that is, a pair of the light loss sections 25 are provided at positions whose distances from the output end 22O are the same, such as the first and second light loss sections 25a and 25b in the first curvature-detecting optical fiber 22a, or the third and fourth light loss sections 25c and 25d in the second curvature-detecting optical fiber 22b. Hereinafter, the position where a pair of the light loss sections 25 is provided is called a "detection point".

The arrangement of the first to fourth light loss sections 25a to 25d is not limited to that in the example represented in FIG. 13. For example, the first and second light loss sections 25a and 25b may be arranged at the same position as each other on the first curvature-detecting optical fiber 22a, the third and fourth light loss sections 25c and 25d may be arranged at the same position as each other on the second curvature-detecting optical fiber 22b, and the distances of the pair of the first and second light loss sections 25a and 25b, and of the pair of the third and fourth light loss sections 25c and 25d, from the output end 22O of the curvature-detecting optical fiber 22, may be different. In any case, how much of the reflected light L is absorbed by each of the first to fourth light loss sections 25a to 25d can be calculated based on the mount of the reflected light received by the first to fourth light-receiving elements 35a to 35d, so that no problem occurs in detecting the configuration of the curvature-detecting optical fiber 22.

Figure 16:
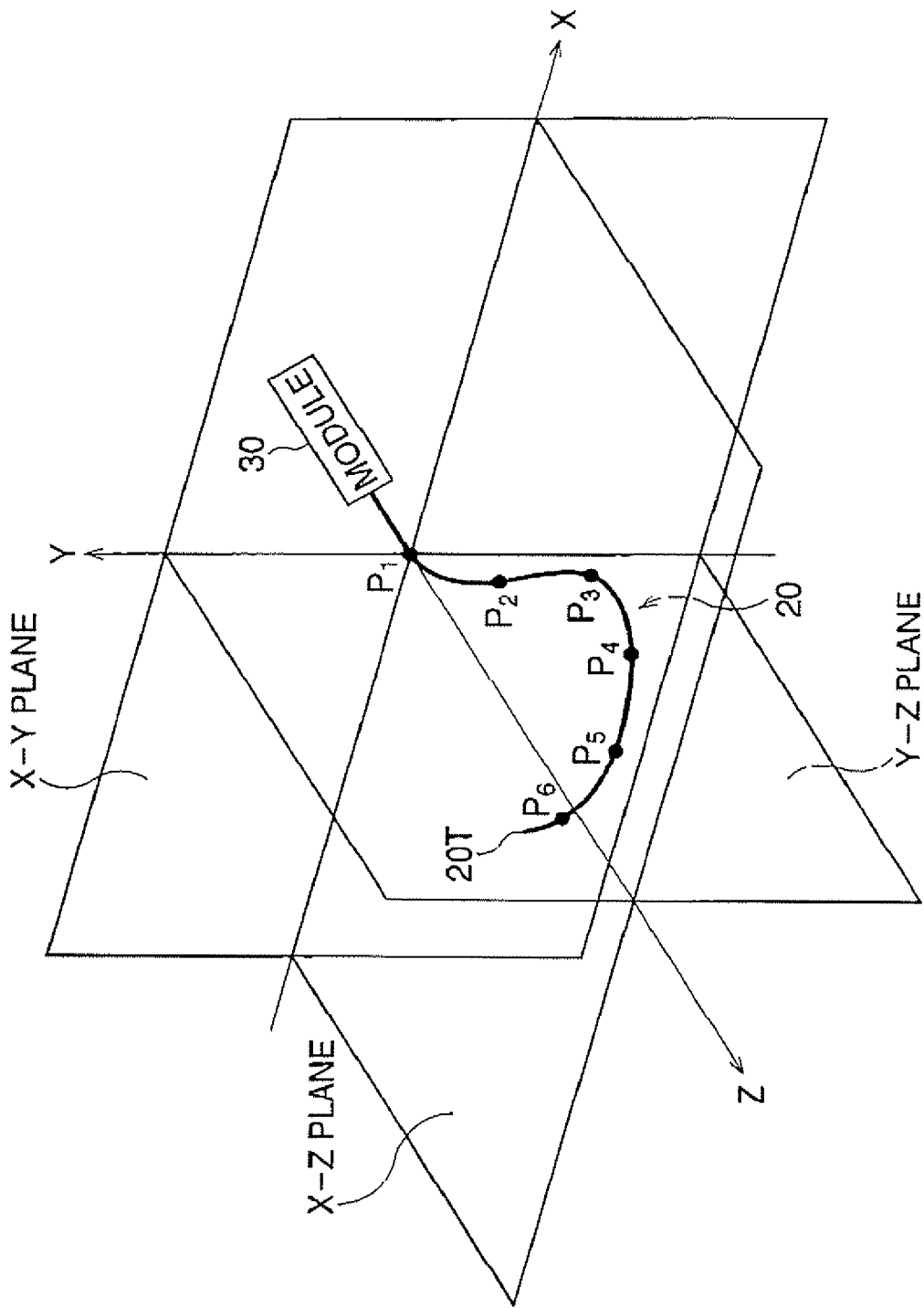
FIG. 16 is a view representing an example of a detected configuration of the fiber bundle.

In the fiber bundle 20, first to sixth detection points $P_1$ to $P_6$ are provided over one interval (see FIG. 16). In the image processing device 60, based on the detected curvatures at the first to sixth detection points $P_1$ to $P_6$, and the previously calculated distances from the output end 22O of the curvature-detecting optical fiber 22 to each of the first to sixth detection points $P_1$ to $P_6$, the configuration of the fiber bundle 20 is drawn. Note that the configuration of the fiber bundle 20 is calculated in a three-dimensional coordinate system where the Z-axis runs in the longitudinal direction of the fiber bundle 20 when pulled straight, and the aforementioned the X-axis and the Y-axis run as in the XY coordinate system (see FIG. 6), as explained below.

Figure 17:
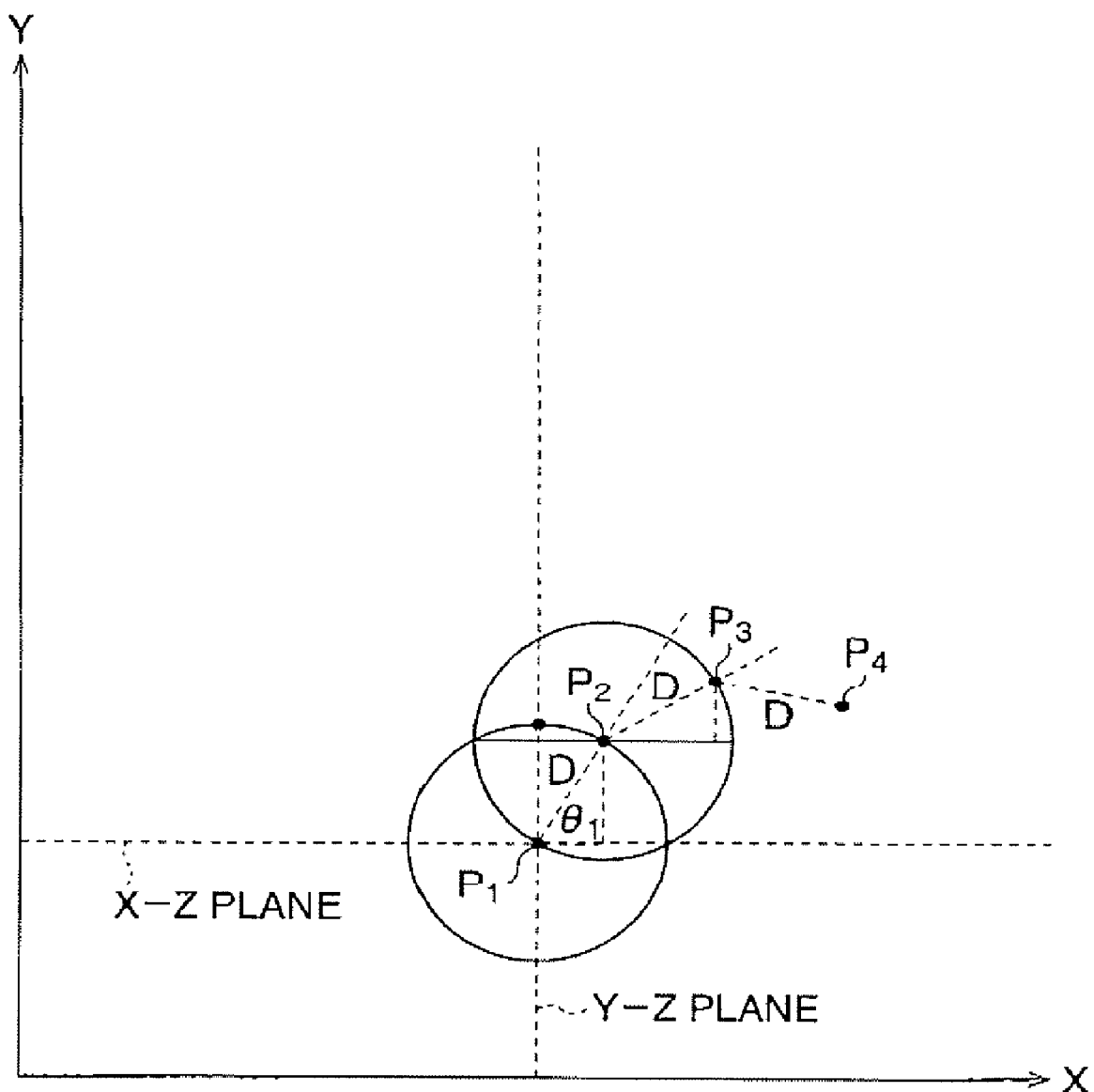
FIG. 17 is a view representing an outline of a method of calculation of curvature at detection points of the fiber bundle.

First, the curvature at the first detection point $P_1$ (see FIG. 16) which is the closest detection point to the light receiving module 30, and which is the origin of the three-dimensional coordinate system, is calculated. The curvature at each detection point is the incline of the extending direction of the fiber bundle 20 against the XY plane at each detection point. Therefore, the curvature $\theta_1$ (see FIG. 17) at the first detection point $P_1$ is calculated based on the curvatures in the X-axis direction and the Y-axis direction, that is, the incline of the extending direction of the fiber bundle 20 against the YZ plane at the first detection point $P_1$ and the incline of the extending direction of the fiber bundle 20 against the XZ plane at the first detection point $P_1$. As explained above, the curvatures in the X-axis direction and in the Y-axis direction are calculated based on the amount of the reflected light L absorbed by the pair of the light loss sections 25. Note that the paper on which FIG. 17 id depicted represents the XY plane of the three-dimensional coordinate system.

The distance D between the first detection point $P_1$ and the second detection point $P_2$ (that is the difference between the distance from the output end 22O of the curvature-detecting optical fiber 22 to the first detection point $P_1$, and the distance between the output end 22O to the second detection point $P_2$) is a predetermined value, and the value is previously input into the image processing device 60 before calculation. Therefore, the position of the second detection point $P_2$ in the three-dimensional coordinate system is determined based on the curvature $\theta_1$ and the distance D. That is, the X-coordinate system value $X_2$ and the Y-coordinate system value $Y_2$ of the second detection point $P_2$ are calculated as in the formulae (1) and (2).

$$X_2 = a \times \cos \theta_1 \quad (1)$$

$$Y_2 = a \times \sin \theta_1 \quad (2)$$

Similarly to with the first and second detection points $P_1$ and $P_2$, regarding the third to sixth detection points $P_3$ to $P_6$, their coordinate system values and their curvatures $\theta$ are calculated. Finally, based on the coordinate system positions and curvatures $\theta_1$ to $\theta_6$ of the first to sixth detection points $P_1$ to $P_6$, the configuration of the fiber bundle 20 is detected and drawn by smoothly connecting the adjacent detection points of the first to sixth detection points $P_1$ to $P_6$. The configuration of the fiber bundle 20 in areas between the detection points $P_1$ to $P_6$ are calculated by approximation, therefore, the accuracy of calculation of the configuration can be improved by providing many detection points P or light loss sections 25.

In the fiber bundle 20 of the first embodiment, laser beams containing different wavelength ranges are provided, and the light loss sections 25 can each absorb one of these laser beams selectively, so plurality of the light loss sections 25 can be provided in one of the light loss sections 25. Therefore, in this embodiment, shortening the diameter of the endoscope detector probe 10 and maintaining a high precision for detecting the configuration of the scope 80 can be achieved.

Note that, although, as in this embodiment, arranging the detection points at equidistant intervals has the advantage of simplifying calculation, the closer the light loss sections 25 are to the end 20T on the mirror 23 side of the fiber bundle 20 (that is, the closer the light loss sections 25 are to the output end of the light-providing optical fiber 21), the shorter may be the distance between the light loss sections 25. The reason is that the insertion section 82 of the scope 80 is designed to have a higher flexibility at the tip side than at the root side, because it is preferable that there be a higher precision for detecting the configuration of the tip side of the fiber bundle 20 which is close to the tip 20T, than the configuration of the other areas of the fiber bundle 20.

In the first embodiment explained above, by providing the light source 44 that emits detection light containing a plurality of wavelength ranges different from one another, and further, by providing a plurality of the light loss sections 25 that each absorb one of the wavelength ranges selectively in the curvature-detecting optical fiber 22, the fiber bundle 20 of the endoscope detector probe 10 can have a narrow diameter and high precision for detecting the configuration of the scope 80.

Figure 18:
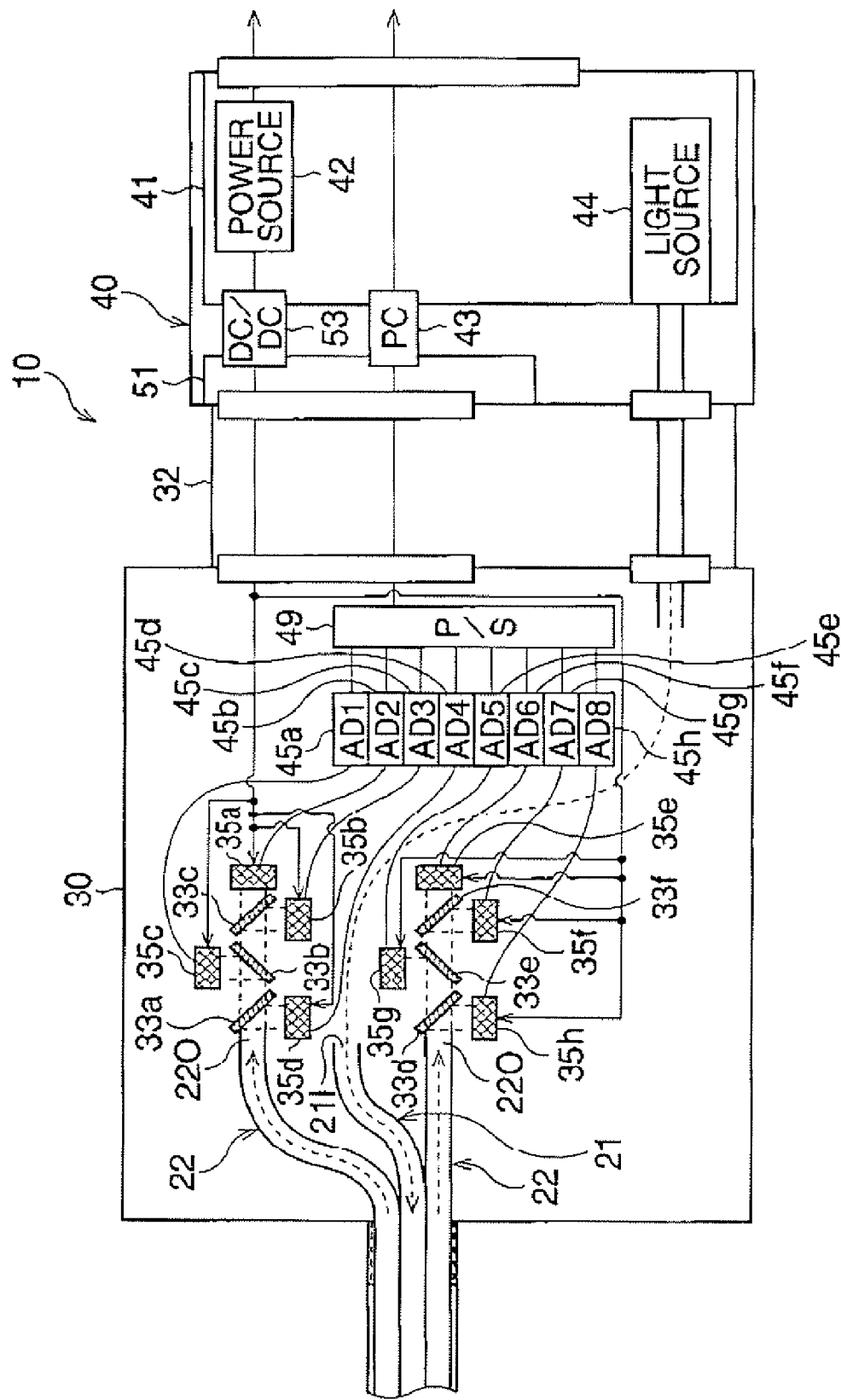
FIG. 18 is a block diagram of a module and a connector of the second embodiment.

Hereinafter, a second embodiment of the present invention is described, mainly focusing on the differences from the first embodiment. In the second embodiment, the light source 44 emits four laser beams each containing a different wavelength range, as the detection light. Therefore, the structure of the light receiving module 30 (see FIG. 18) is more complex than that in the first embodiment, The reason is that, since the reflected light L transmitted by one of the curvature-detecting optical fibers 22 needs to be decomposed into four wavelength ranges, it is required that, for two curvature-detecting optical fibers 22, there be first to sixth dichroic mirrors 33a to 33f, first to eighth light-receiving elements 35a to 35h, and first to eighth A/D converters 45a to 45h.

Because the laser beam containing four wavelength ranges enters each of the curvature-detecting optical fibers 22, in the second embodiment (see FIG. 19), four corresponding light loss sections 25 are provided in each of the curvature-detecting optical fibers 22. By providing the same number of light loss sections 25 as the number of wavelength ranges, the accuracy for detecting the configuration of the fiber bundle 20 can be improved and also narrowing the diameter of the endoscope detector probe 10 can be achieved. The wavelengths of the reflected light L absorbed by the different coating materials 28 coated in the light loss sections 25 are each different, just as in the first embodiment. That is, each of the light loss sections 25 selectively absorbs one of the four wavelength ranges which are different from one another, and which are all contained in the detection light Therefore, the curvature can be calculated for each of the light loss sections 25.

Figure 19:
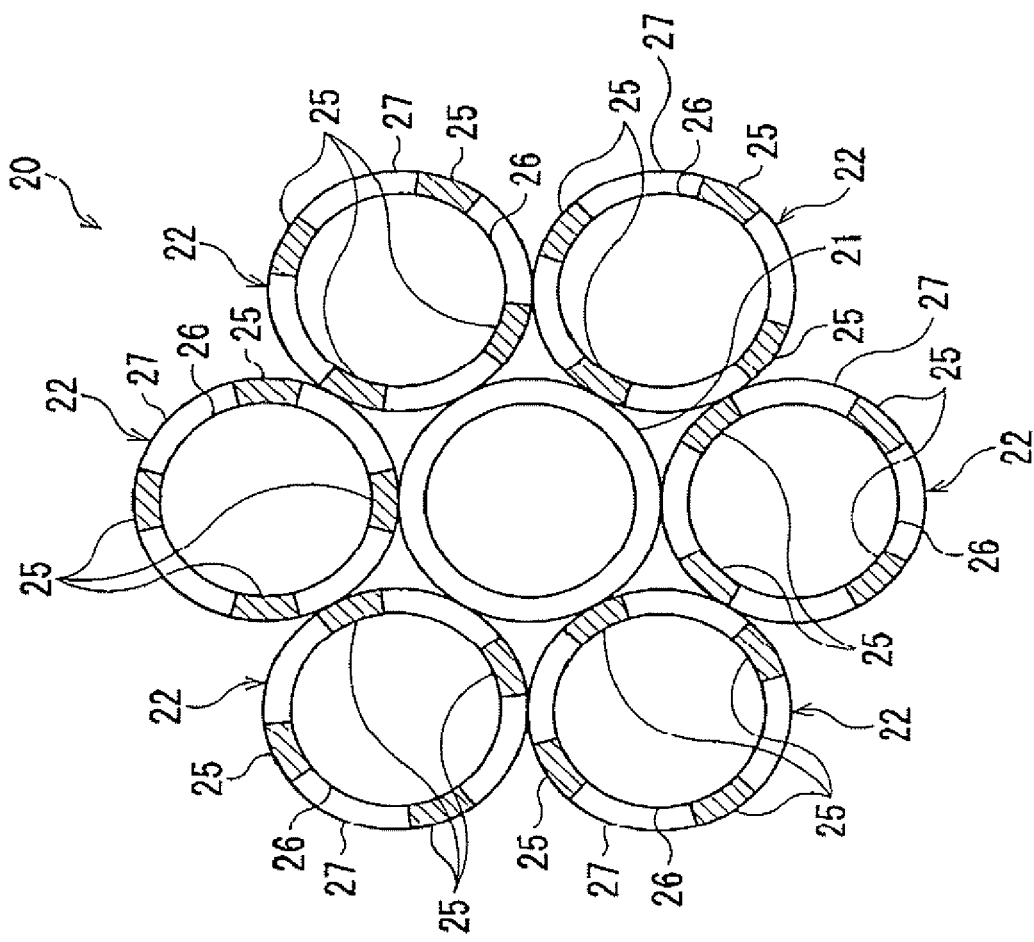
FIG. 19 is a sectional view of the fiber bundle of the second embodiment at the light loss section, taken along a perpendicular direction to the longitudinal direction thereof.

Note that the light loss sections 25 may be arranged on various positions of the fiber bundle 20 in practice, although to simplify description, all of the light loss sections 25 are depicted as on the same section in FIG. 19, just as in the corresponding FIG. 6.

Figure 20:
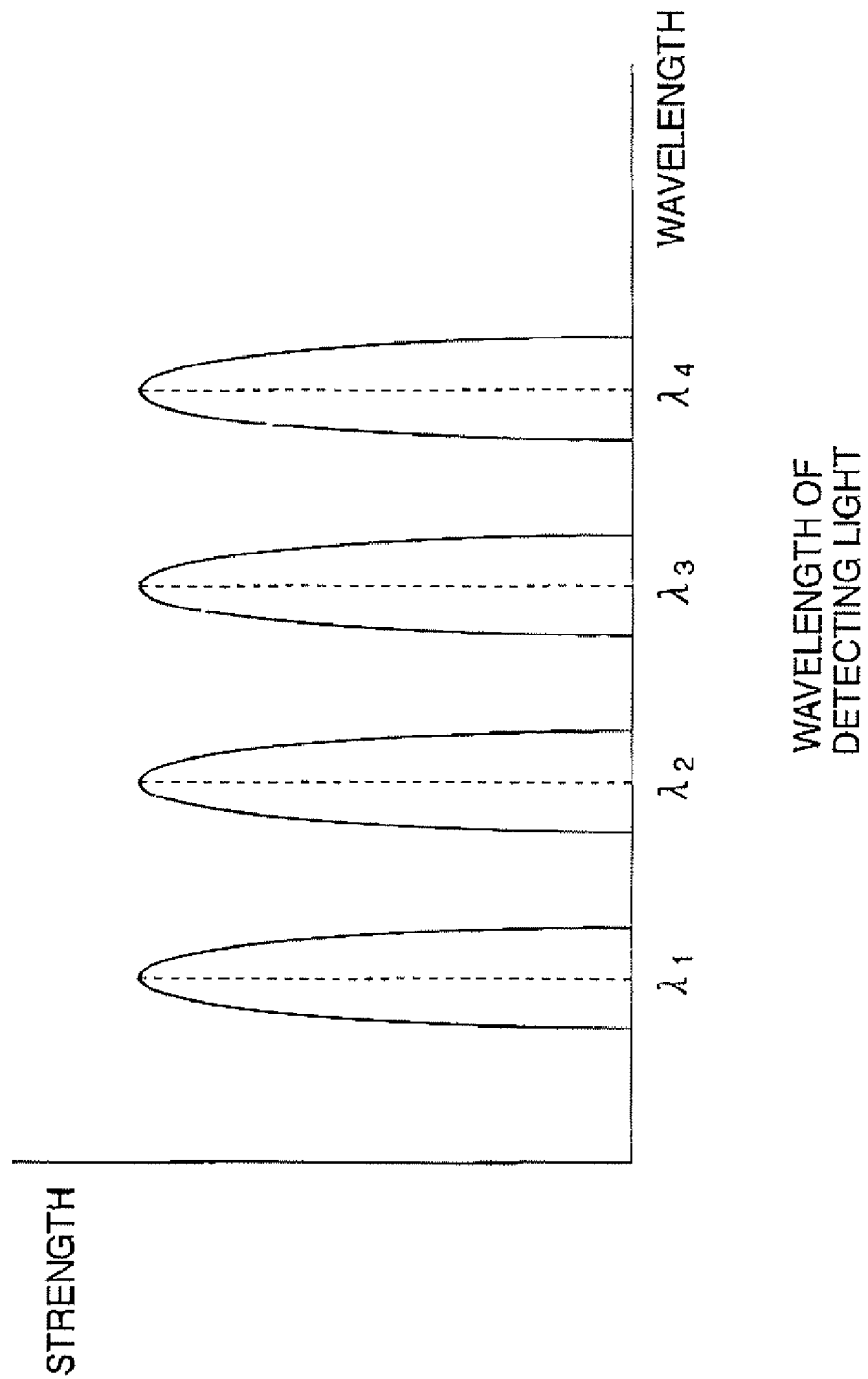
FIG. 20 is a graph representing the wavelength and strength of detection light that is emitted by the light source of the second embodiment.
Figure 21:
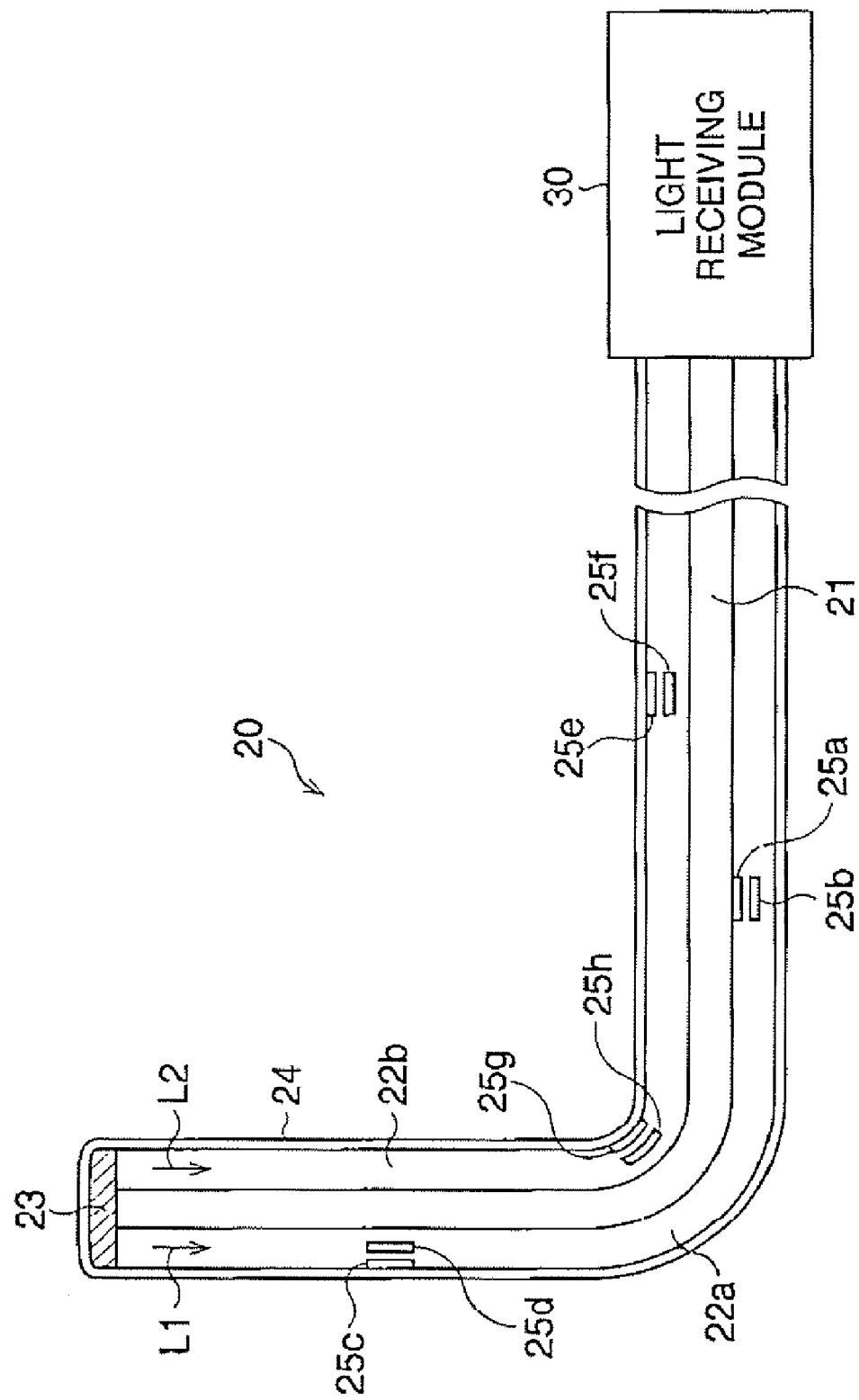
FIG. 21 is a sectional view of the fiber bundle of the second embodiment that is in the bent state, taken along a surface that runs through the center of the fiber bundle, and that extends in a longitudinal direction of the fiber bundle.

As represented in FIG. 20, the light source 44 emits the detection light in four wavelength ranges, which are centered on the unique wavelengths $\lambda_1$ to $\lambda_4$; that is, the detection light contains the first to fourth laser beams. As shown in FIG. 21, in the first curvature-detecting optical fiber 22a, the first to fourth light loss sections 25a to 25d are provided. Further, in the second curvature-detecting optical fiber 22b, the fifth to eighth light loss sections 25e to 25h are provided. The first and fifth light loss sections 25a and 25e selectively absorb the first laser beam, which has a wavelength range centered on the wavelength $\lambda_1$. Similarly, the second and sixth light loss sections 25b and 25f selectively absorb the second laser beam which has a wavelength range centered on the wavelength $\lambda_2$, the third and seventh light loss sections 25c and 25g selectively absorb the third laser beam, which has a wavelength range centered on the wavelength $\lambda_3$, and the fourth and eighth light loss sections 25d and 25h selectively absorb the fourth laser beam, which has a wavelength range centered on the wavelength $\lambda_4$.

The first and second reflected lights $L_1$ and $L_2$ which have the same components as each other (that is, the first and second reflected lights $L_1$ and $L_2$ which contain the first to fourth laser beams in the same ratio, and which have same strength) enter the first and second curvature-detecting optical fibers 22a and 22b, respectively. At that time, the first curvature-detecting optical fiber 22a is not bent where the first to fourth light loss sections 25a to 25d are provided. Therefore, the first reflected light $L_1$ passes through the first curvature-detecting optical fiber 22a without loss in strength.

Next, the absorption of the reflected light in the second curvature-detecting optical fiber 22b is explained below The second curvature-detecting optical fiber 22b is straight where the fifth and sixth light loss sections 25e and 25f are provided. Therefore, the wavelength ranges centered on the wavelengths $\lambda_1$ and $\lambda_2$ of the second reflected light $L_2$ that may be absorbed by those fifth and sixth light loss sections 25e and 25f are not absorbed.

On the other hand, the second curvature-detecting optical fiber 22b is curved where the seventh and eighth light loss sections 25g and 25h are provided. The second curvature-detecting optical fiber 22b is curved where the direction of the curvature is the subject of the detection by the seventh light loss section 25g. Therefore, the third laser beam containing the wavelength range centered on the wavelength $\lambda_3$ is absorbed by the seventh light loss section 25g (see FIG. 22). On the other hand, the eighth light loss section 25h that makes a pair with the seventh light loss section 25g, and that is included at the same detection point, is provided for detecting the curvature of the second curvature-detecting optical fiber 22b in the direction perpendicular to the subject direction of the eighth light loss section 25h, so that the eighth light loss section 25h does not absorb the fourth laser beam, when the second curvature-detecting optical fiber 22b is bent as represented in FIG. 21.

In the second embodiment explained above, the light source 44 that emits detection light in four unique wavelength ranges, outnumbering those in the first embodiment, is provided, so that four light loss sections 25 and two detection points can be provided on each one of the curvature-detecting optical fibers 22. Therefore, more precise detection of the configuration of the scope 80 can be achieved by the endoscope detector probe 10 with the fiber bundle 20 in the second embodiment than those in the first embodiment.

In the second embodiment, the diameter of the fiber bundle 20 may be further narrowed. For example, in a case where six detection points are provided over the entire fiber bundle 20, to obtain the same detection precision as that in the first embodiment, only three curvature-detecting optical fibers 22, each having two detection points, are required. Therefore, the diameter of the fiber bundle 20 can be narrowed.

Note that the structures of the endoscope detector probe 10 and of the fiber bundle 20 and other components are not limited to those in both embodiments, For example, a light source 44 that emits detection light in three different wavelengths, and a curvature-detecting optical fiber 22c with three light loss sections 25 that each selectively absorb one of the wavelengths, may alternatively be provided (see FIG. 23).

Instead of the light loss sections 25 that use the coating material 28 that absorbs one of the wavelength ranges of the reflected light of the detection light, different types of light modulators may be formed by a material that absorbs one of the wavelength ranges of the light, and that emits light in different wavelength ranges. In such a case, the same numbers of light modulators as the numbers of wavelength ranges of detection light are provided on one of the curvature-detecting optical fibers 22. Each of the light modulators absorbs one of wavelength ranges which are different from one another, selectively, and then emit the reflected light in wavelength ranges where one of the wavelength ranges is different from the corresponding pre-modulated wavelength, and where all of the wavelength ranges are different from each other.

For such a material, for example, a fluorescent material that emits light having a longer wavelength than that of the absorbed light can be used. In such a case, the curvature at the detection point is detected based on the degree that the wavelength range of the reflected light L that has passed through the light modulator varies; that is, it is detected based on the difference of the wavelength ranges pre-modulated and post-modulated.

Note that a light source that emits light in a plurality of independent wavelength ranges (that is, in a plurality of wavelength ranges that do not overlap, with one another), using a filter or other components, may be used, instead of the light source 44. Alternatively, a white light source that emits white light consisting of independent wavelength ranges by composing a plurality of wavelength components my also be used.

The number of light loss sections 25 provided in the curvature-detecting optical fiber 22 may be smaller that the number of wavelength ranges of the detection light emitted by the light source 44, although it is advantageous if it is the same as the number of wavelength ranges, to improve the detection precision and narrow the diameter of the fiber bundle.

This invention is not limited to that described in the preferred embodiments; namely, various improvements and changes may be made to the present invention without departing from the spirit, and scope thereof.

The present disclosure relates to subject matter contained in Japanese Patent Application No 2005-338528 (filed on Nov. 24, 2005), which is expressly incorporated herein, by reference, in its entirety.

The invention claimed is:

1. A configuration detection device for detecting a configuration of an endoscope, said configuration detection device comprising:
 a light-providing optical fiber that transmits detection light in a plurality of wavelength ranges that differ from one another;
 a light reflector that reflects said detection light as reflected light, in a same reflection ratio as for said wavelength ranges, said light reflector being provided at an output end of said light-providing optical fiber;
 a curvature-detecting optical fiber that transmits said reflected light, said curvature-detecting optical fiber being bent together with said endoscope; and
 a light modulator that modulates at least one of a strength and a wavelength of said reflected light for each of said wavelength ranges, said light modulator being provided in said curvature-detecting optical fiber,
 wherein said configuration of said endoscope is detectable, based on at least one of the strength and the wavelength of said reflected light that is pre-modulated and post-modulated, and based on a distance between said light modulator and an output end of said curvature-detecting optical fibers,
 wherein a plurality of said light modulators are provided at equidistant positions from the output end of said curvature-detecting optical fiber, and
 wherein at least a pair of said plurality of light modulators are provided to form a right angle by said light modulators and a center point of said curvature-detecting optical fiber.

2. The configuration detection device according to claim 1, wherein said light modulator absorbs a portion of said reflected light.

3. The configuration detection device according to claim 1, wherein a number of said light modulators provided in said curvature-detecting optical fibers is equal to a number of said wavelength ranges of said detection light.

4. The configuration detection device according to claim 1, wherein the proximity of said light modulators to the output end of said light-providing optical fiber is directly proportional to the distance between said light modulators.

5. The configuration detection device according to claim 1, wherein a plurality of said curvature-detecting optical fibers are arranged around said light-providing optical fiber.

6. The configuration detection device according to claim 1, wherein said light modulator modulates said reflected light so that said wavelength ranges that are modulated have different wavelengths from one another.

7. The configuration detection device according to claim 1, further comprising a light source that emits said detection light, and a light detector that detects at least one of the strength and the wavelength of each of said wavelength ranges that are modulated.

8. A configuration detection system for detecting a configuration of an endoscope, said configuration detection system comprising:
 a light source that emits detection light containing a plurality of wavelength ranges that differ from one another;
 a fiber bundle comprising:
  a light-providing optical fiber that transmits said detection light;
  a light reflector that reflects said detection light as reflected light, in a same reflection ratio as for said wavelength ranges, said light reflector being provided at an output end of said light-providing optical fiber;
  a curvature-detecting optical fiber that transmits reflected light of said detection light, said curvature-detecting optical fiber being bent together with said endoscope; and
  a light modulator that modulates at least one of a strength and a wavelength of said reflected light for each of said wavelength ranges, said light modulator being provided in said curvature-detecting optical fiber;
 a light detector that detects at least one of the strength and the wavelength of each of said wavelength ranges that are modulated;
 a configuration detector that detects said configuration of said endoscope, based on the strength and the wavelength of said reflected light that is pre-modulated and post-modulated, and based on at least one of a distance between said light modulator and the output end of said curvature-detecting optical fiber; and
 an image display that displays an image representing said configuration of said endoscope that is detected wherein a plurality of said light modulators are provided at equidistant positions from the output end of said curvature-detecting optical fiber, and wherein at least a pair of said plurality of light modulators are provided to form a right angle by said light modulators and a center point of said curvature-detecting optical fiber.

9. The configuration detection device according to claim 1, wherein said light modulators are provided on a line parallel to one of an X-axis and a Y-axis of a coordinate system for calculating a curvature, when said curvature-detecting optical fiber is in a straight state.

10. The configuration detection device according to claim 1, wherein said plurality of light modulators are grouped in pairs, each of the pairs being provided at positions equidistant from each other along the output end of said curvature-detecting optical fiber.

11. The configuration detection system according to claim 8, wherein said light modulators are provided on a line parallel to one of an X-axis and a Y-axis of a coordinate system for calculating a curvature, when said curvature-detecting optical fiber is in a straight state.

12. The configuration detection system according to claim 8, wherein said plurality of light modulators are grouped in pairs, each of the pairs being provided at positions equidistant from each other along the output end of said curvature-detecting optical fiber.

* * * * *